US012649901B2

(12) United States Patent
Marushima et al.

(10) Patent No.: US 12,649,901 B2
(45) Date of Patent: Jun. 9, 2026

(54) NERVE BUNDLE AND PRODUCTION METHOD OF NERVE BUNDLE

(71) Applicant: UNIVERSITY OF TSUKUBA, Tsukuba (JP)

(72) Inventors: Aiki Marushima, Tsukuba (JP); Akira Matsumura, Tsukuba (JP); Hiroki Bukawa, Tsukuba (JP); Yuji Matsumaru, Tsukuba (JP); Masao Koda, Tsukuba (JP); Hiroshi Ishikawa, Tsukuba (JP); Akihiro Ohyama, Tsukuba (JP); Junko Toyomura, Tsukuba (JP); Shohei Takaoka, Tsukuba (JP); Yosuke Shibao, Tsukuba (JP); Miho Watanabe, Tsukuba (JP); Tetsuya Abe, Tsukuba (JP)

(73) Assignee: University of Tsukuba, Tsukuba (JP)

( * ) Notice: Subject to any disclaimer, the term of this patent is extended or adjusted under 35 U.S.C. 154(b) by 531 days.

(21) Appl. No.: 17/478,271

(22) Filed: Sep. 17, 2021

(65) Prior Publication Data

US 2022/0106561 A1     Apr. 7, 2022

(30) Foreign Application Priority Data

Sep. 18, 2020    (JP) ................................. 2020-157621

(51) Int. Cl.
| | | |
|---|---|---|
| *C12N 5/0793* | (2010.01) | |
| *A61L 27/36* | (2006.01) | |
| *A61L 27/38* | (2006.01) | |
| *C12M 3/00* | (2006.01) | |

(52) U.S. Cl.
CPC ........ *C12N 5/0619* (2013.01); *A61L 27/3675* (2013.01); *A61L 27/383* (2013.01); *C12M 21/08* (2013.01); *C12N 2501/11* (2013.01); *C12N 2501/115* (2013.01); *C12N 2501/13* (2013.01); *C12N 2501/165* (2013.01); *C12N 2533/90* (2013.01)

(58) Field of Classification Search
CPC .............. C12N 5/0619; C12N 2501/11; C12N 2501/115; C12N 2501/13; C12N 2501/165; C12N 2533/90; C12N 5/069; C12N 2506/1361; A61L 27/3675; A61L 27/383; A61L 2300/64; A61L 2430/32; A61L 27/3808; A61L 27/3826; A61L 27/3878; C12M 21/08; C12M 23/12
See application file for complete search history.

(56) References Cited

U.S. PATENT DOCUMENTS

2019/0127672 A1* 5/2019 Fujii ...................... C12M 23/12

FOREIGN PATENT DOCUMENTS

| | | | |
|---|---|---|---|
| JP | 2014-136128 A | | 7/2014 |
| JP | 2017079704 A | * | 5/2017 |
| JP | 2019-000093 A | | 1/2019 |
| JP | 2019-154331 A | | 9/2019 |
| WO | WO-2017-187696 A1 | | 11/2017 |

OTHER PUBLICATIONS

Osaki, T., Sivathanu, V. and Kamm, R.D., 2018. Engineered 3D vascular and neuronal networks in a microfluidic platform. Scientific reports, 8(1), p. 5168. (Year: 2018).*
Larrivée, B., Freitas, C., Suchting, S., Brunet, I. and Eichmann, A., 2009. Guidance of vascular development: lessons from the ner (Year: 2009).*
Abe et al., "Transplantation of axon-like nerve bundles derived from nerve stem cells derived from the subepithelial layer of the gingiva to promote spinal cord regeneration," KAKEN 2018 Fiscal Year Implementation-States Report, Dec. 27, 2019, Research Subject/Field No. 18K08989, with English translation, 4 pages.
Office Action dated Nov. 19, 2024 in JP 2020-157621, with English machine translation.

* cited by examiner

*Primary Examiner* — Jeremy C Flinders
*Assistant Examiner* — Masudur Rahman
(74) *Attorney, Agent, or Firm* — Foley & Lardner LLP

(57) ABSTRACT

The object of this invention is to provide a method of producing a nerve bundle including efficiently extending axons of neural cells. As a solution to accomplish this end, neural cells are cultivated in the presence of feeder cells including at least one type of cells selected from vascular component cells and perivascular cells.

27 Claims, 17 Drawing Sheets

FIG. 6A
FIG. 6B
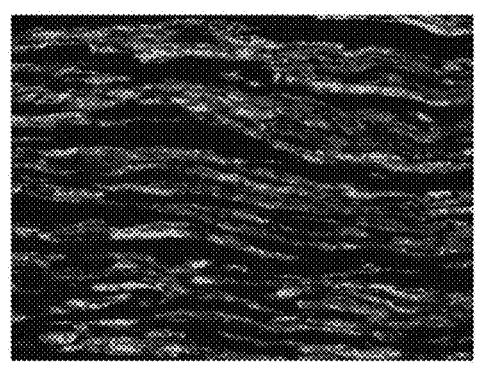
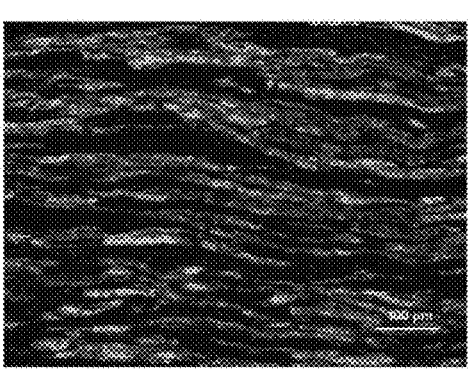
FIG. 6C
FIG. 6D

NF200/MBP/DAPI

FIG. 9A                                    FIG. 9B

NF200/S100                              S100/PERIPHERIN

NF200/PERIAXIN/DAPI

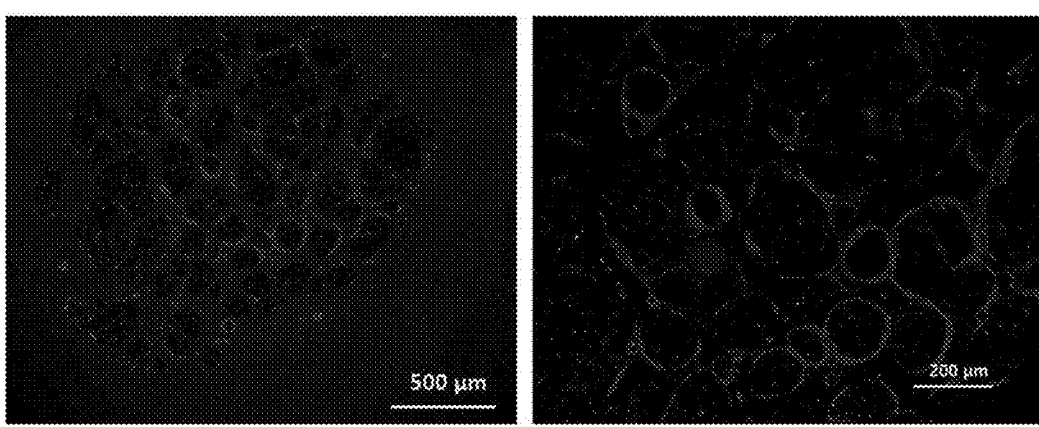
FIG. 11A                    FIG. 11B

CD31/PDGFRβ/DAPI
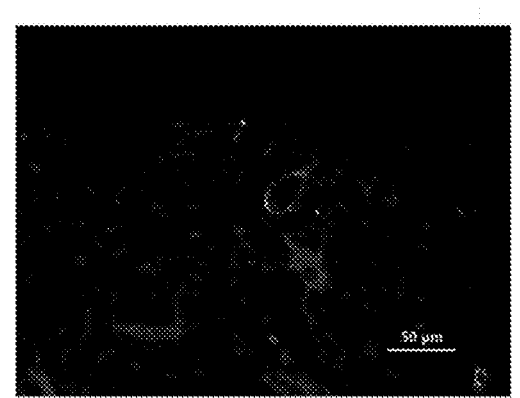
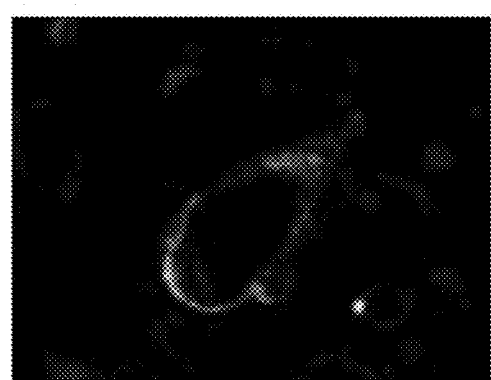
FIG. 12A                      FIG. 12B

CD31/PDGFRβ/DAPI

FIG. 14A
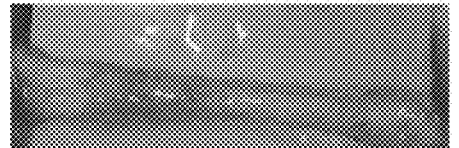
FIG. 14C
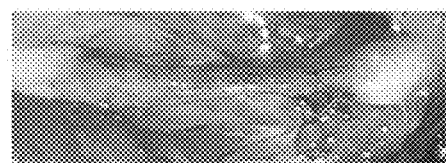
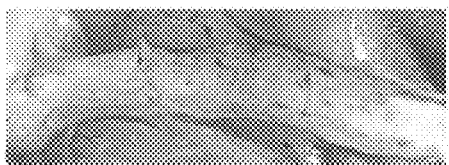
FIG. 14B
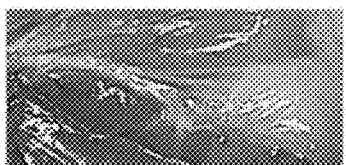
FIG. 14D

FIG. 15A

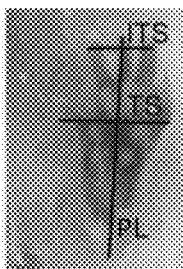

SFI=-38.3 × [(EPL-NPL)/NPL]+109.5 × [(ETS-NTS)/NTS]+13.3 × [(EITS-NITS)/NITS]-8.8

EPL: experimental print length
NPL: normal print length
ETS: experimental toe spread
NTS: normal toe spread
EITS: experimental intermediary toe spread
NITS: normal intermediary toe spread 0 ~ -11% : normal nerve function
-11 ~ -100% : incomplete damage of nerve function
-100% : complete damage of nerve function

FIG. 15B

SFI (SCIATIC FUNCTIONAL INDEX)

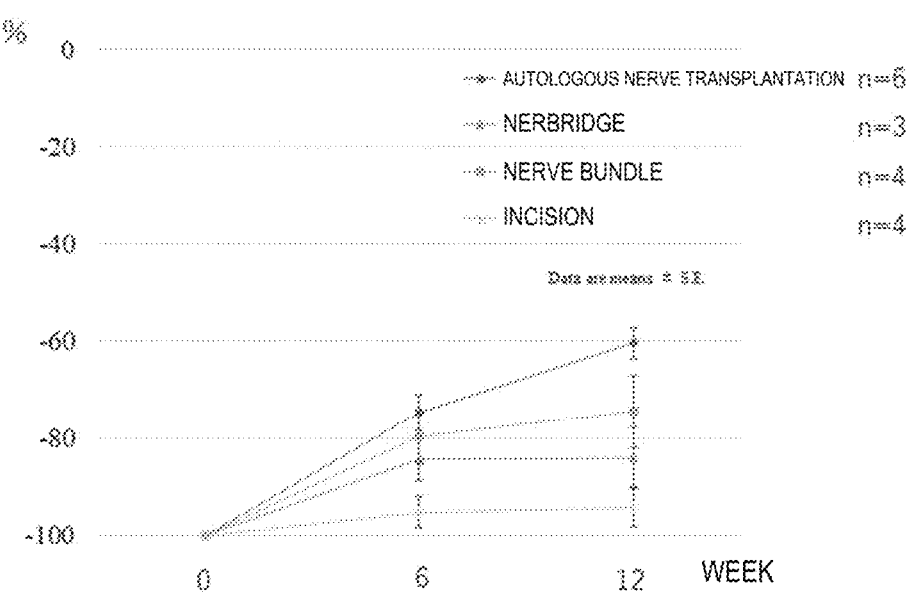

STEM121/p75NTR/MPZ/DAPI
FIG. 17A                                    FIG. 17B
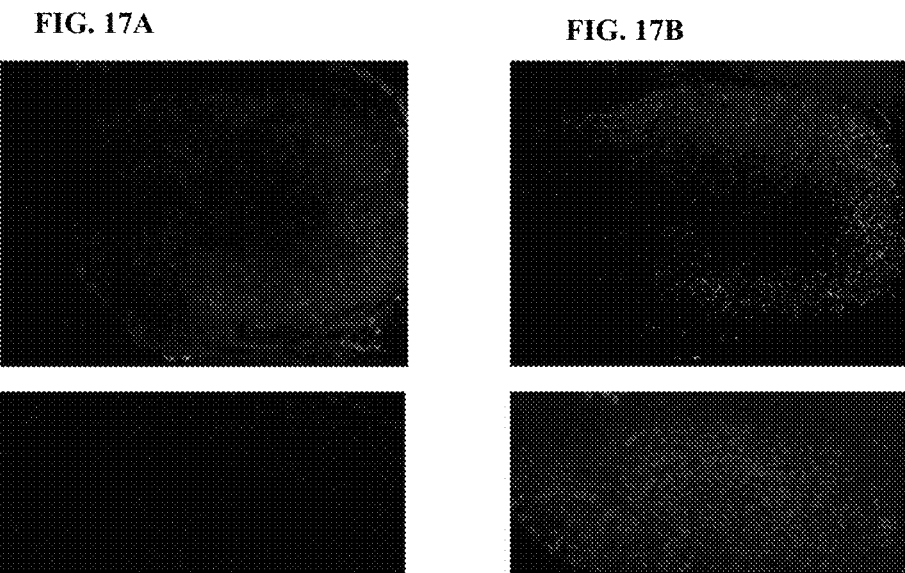
FIG. 17C                                    FIG. 17D
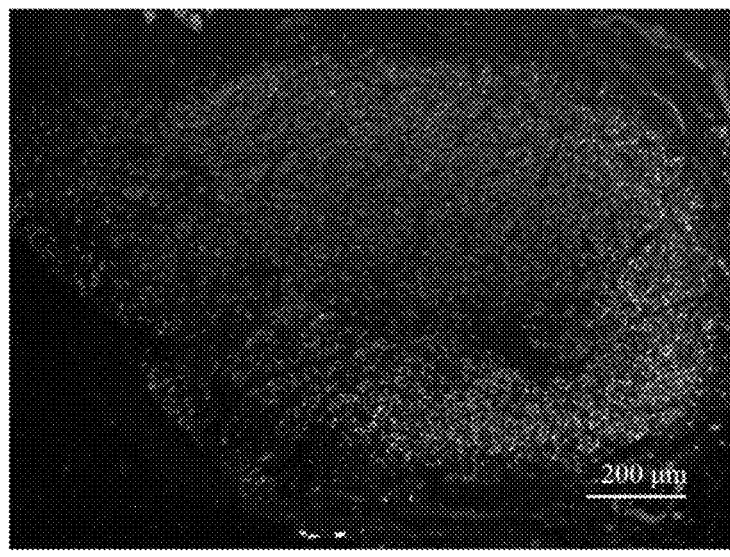
FIG. 17E

NERVE BUNDLE AND PRODUCTION METHOD OF NERVE BUNDLE

CROSS-REFERENCE TO RELATED APPLICATIONS

This application claims priority to JP 2020-157621, filed Sep. 18, 2020.

TECHNICAL FIELD

The present invention relates to a nerve bundle and a method of producing a nerve bundle.

BACKGROUND ART

In recent years, methods of transplanting nerves have been developed to restore the function of nerves that had been damaged due to neurodegenerative diseases and physical causes. As a method of transplanting nerves, widely used is a method of injecting neural stem cells into the affected part by injection. However, this method has an issue that injected neural stem cells tend to move inside the body and are less likely to be engrafted, and thus it is difficult to efficiently repair the damaged site in neural tissues such as brain, spinal cord, complex peripheral nerves.

In order to solve this issue, methods have been developed for joining a bundle of neurons (nerve bundle) with extended axons to the remaining nerves at the damaged site and transplanting such a bundle. As a method for obtaining a nerve bundle for transplantation, methods for cultivating neural cells so that axons of neurons extend so as to form a nerve bundle have been reported (Patent Documents 1 and 2). In these methods, there has been an issue that the axons of neurons cannot be efficiently extended and enlarged, and it is difficult to obtain a nerve bundle including axons having a length and a thickness (diameter) sufficient for implantation.

Under such circumstances, there is a need for a method in which a nerve bundle including axons having a length and a diameter sufficient for transplantation can be efficiently obtained.

CITATION LIST

Patent Literature

Patent Document 1: WO 2017-187696 A
Patent Document 2: JP 2014-136128 A
The present inventors have found that, as a result of cultivation of neural cells using predetermined cells as feeder cells, axons of neural cells can be efficiently extended. The present inventors have also found that the axons can be enlarged as the extension of axons of neural cells. According to the present invention, it is possible to efficiently form a nerve bundle including axons having a length and a diameter sufficient for transplantation. The present invention is based on these findings.

The present invention includes the following invention.

[1] A method of producing a nerve bundle, the method including cultivating a neural cell-containing cell population in the presence of at least one type of feeder cells selected from vascular component cells and perivascular cells to extend axons of neural cells.

[2] The method according to [1], in which the feeder cells include at least one type of cells selected from the group consisting of pericytes, vascular endothelial cells, fibroblasts, smooth muscle cells, oligodendrocytes, and Schwann cells.

[3] The method according to [1] or [2], in which the feeder cells include cells secreting at least one type of growth factor selected from the group consisting of VEGF, NGF, BDNF, FGF-2, NGFB, and EGF.

[4] The method according to any one of [1] to [3], in which the nerve bundle includes a myelin sheath containing Schwann cells.

[5] The method according to any one of [1] to [4], including:
(a) preparing a substrate including at least one recess and a channel portion connected to the recess, the channel portion being covered with the feeder cells;
(b) adding the neural cell-containing cell population to the recess; and
(c) cultivating the neural cell-containing cell population to extend axons of neural cells along the channel portion.

[6] The method according to any one of [1] to [5], including:
(a) preparing a substrate including two recesses and a channel portion connecting the two recesses, the channel portion being covered with the feeder cells;
(b) adding the neural cell-containing cell population to the recesses; and
(c) cultivating the neural cell-containing cell population to extend axons of neural cells along the channel portion.

[7] The method according to [5] or [6], in which, in the step (a), the channel portion is covered with fibroblasts before covered with the feeder cells.

[8] The method according to any one of [1] to [7], in which the neural cell-containing cell population further includes endothelial cells.

[9] The method according to [8], in which the endothelial cells included in the neural cell-containing cell population are blood vessel-derived endothelial cells.

[10] The method according to [9], in which the blood vessel-derived endothelial cells are blood vessel-derived endothelial cells in at least one tissue selected from the group consisting of a pulp, a gingiva, a subcutaneous tissue, a coelomic artery, a coelomic vein, and an umbilical cord.

[11] The method according to any one of [8] to [10], further including, in the step (c), forming a tube derived from endothelial cells in the neural cell-containing cell population.

[12] The method according to any one of [8] to [11], in which the neural cells and the endothelial cells are derived from an identical individual.

[13] The method according to any one of [8] to [12], in which the neural cell-containing cell population further includes a biocompatible material, and the neural cells and the endothelial cells are each layered on surfaces of different biocompatible materials.

[14] The method according to [13], in which the biocompatible material includes a collagen.

[15] The method according to [13] or [14], in which the biocompatible material includes collagen beads.

[16] The method according to any one of [5] to [15], in which the channel portion has a length of 3 mm or greater.

[17] A nerve bundle produced by the method described in any one of [1] to [16].

[18] A method of producing an implant including covering a nerve bundle with a sheet of a biocompatible material, the nerve bundle being produced by the method described in any one of [1] to [16].

[19] The method according to [18], in which the sheet includes fibroblasts.

The method according to [18] or [19], in which the implant is a nerve regeneration implant.

[21] An implant produced by the method described in any one of [18] to [20].

[22] A method of extending axons of neural cells, the method including cultivating neural cells in the presence of feeder cells including at least one type of cells selected from vascular component cells and perivascular cells.

[23] The method according to [22], in which the feeder cells include at least one type of cells selected from the group consisting of pericytes, endothelial cells, fibroblasts, smooth muscle cells, oligodendrocytes, and Schwann cells.

[24] A nerve bundle including: neural cells with extended axons; and a tube of endothelial cells present along the axons, in which the nerve bundle includes at least one type of cells selected from HNK-1 carbohydrate-expressing cells and p75NTR-expressing cells.

[25] The nerve bundle according to [24], including HNK-1 carbohydrate-expressing cells and p75NTR-expressing cells.

[26] The nerve bundle according to [24] and [25], including at least one type of cells selected from the group consisting of NS200-expressing cells, peripherin-expressing cells, myelin basic protein-expressing cells, S100-expressing cells, MPZ-expressing cells, periaxin-expressing cells, CD31-expressing cells, and PDGFRβ-expressing cells.

[27] The nerve bundle according to any one of [24] to [26], including: NS200-expressing cells; peripherin-expressing cells; myelin basic protein-expressing cells; S100-expressing cells; MPZ-expressing cells; periaxin-expressing cells; CD31-expressing cells; and PDGFRβ-expressing cells.

[28] The nerve bundle according to any one of [24] to [27], including a cell layer including at least one cell selected from fibroblasts and pericytes that cover, along the axons of the neural cells, at least some of the axons, in which the tube of endothelial cells is present in the cell layer.

[29] The nerve bundle according to any one of [24] to [28], in which the tube of endothelial cells further includes pericytes.

[30] An implant including the nerve bundle described in any of [24] to [29].

[31] The implant according to [30], which is a nerve regeneration implant.

The present invention makes it possible to extend axons of neural cells efficiently. Also, the present invention makes it possible to enlarge the axons of neural cells efficiently. Further, the present invention makes it possible to form a nerve bundle having axons with a length and diameter sufficient for transplantation efficiently. Furthermore, the present invention makes it possible for a nerve bundle to be obtained, the nerve bundle including neural cells and a tube of endothelial cells present along the axons of the neural cells.

4

Figure 4A:
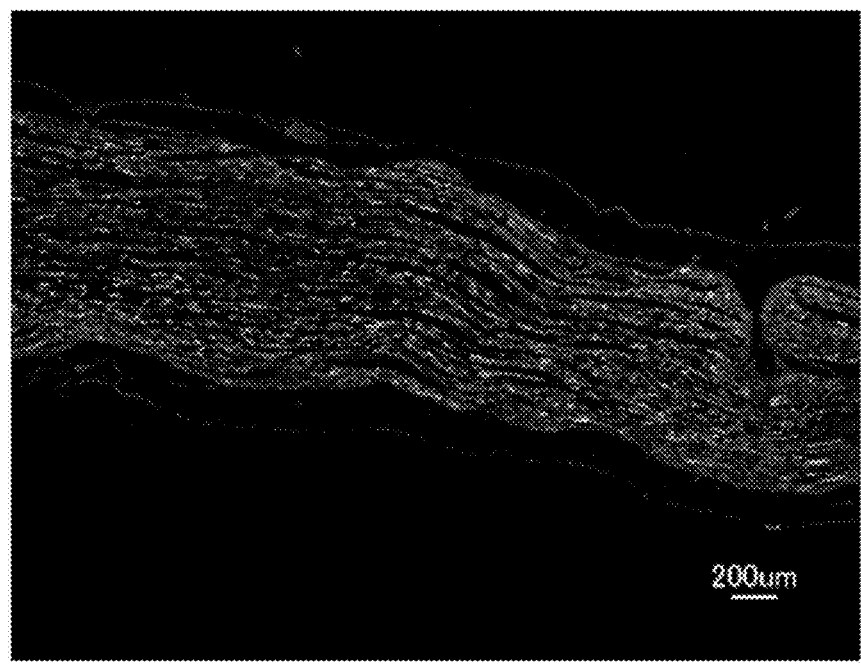
Figure 4B:
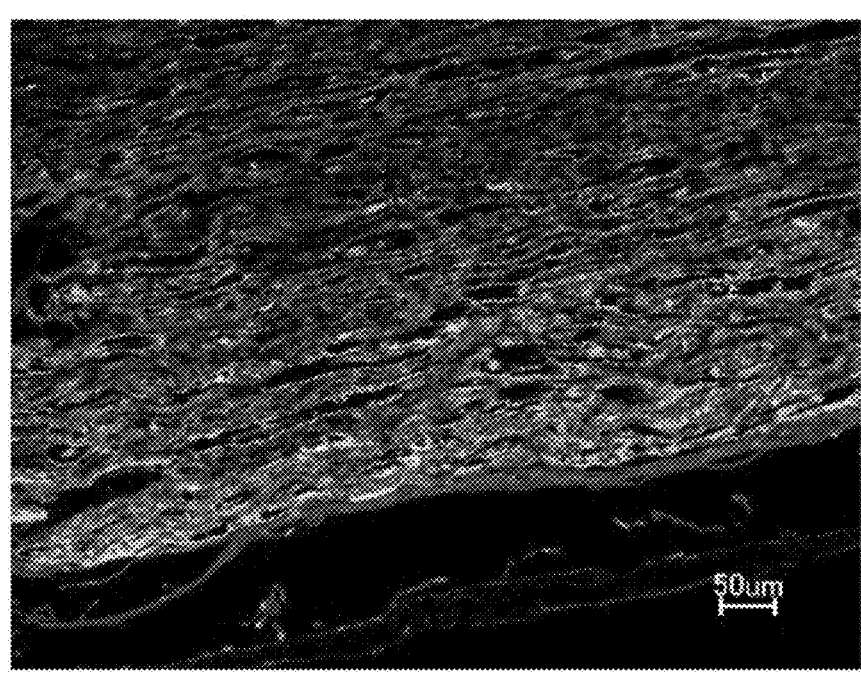

FIGS. 4A to 4B are images of immunostaining of a nerve bundle formed by a method in Examples. FIG. 4A is a photograph of immunostaining using an anti-vWF antibody and an anti-F200 antibody. FIG. 4B is a photograph of immunostaining using an anti-vWF antibody and an anti-S100 antibody.

Figure 5A:
Figure 5B:
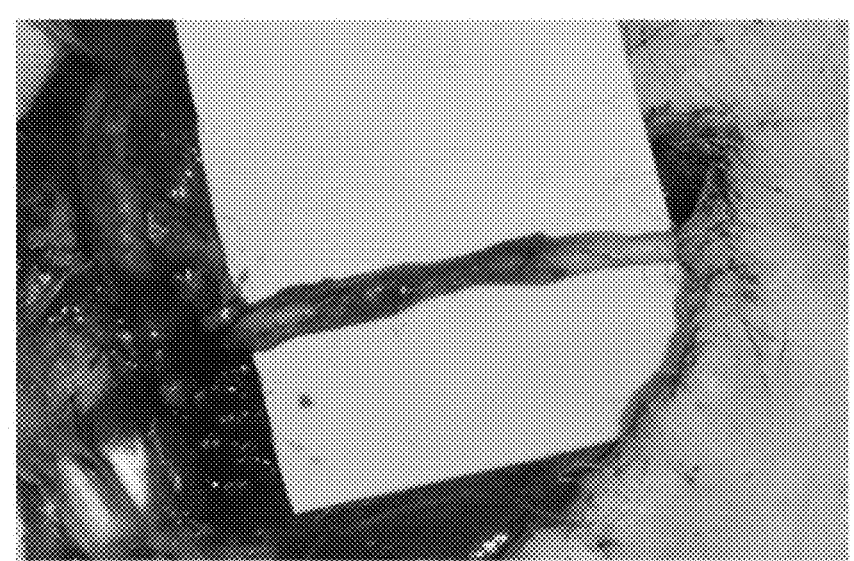

FIG. 5A is a photograph of a transplanted site immediately after transplantation of a nerve bundle implant into the sciatic nerve of a rat. FIG. 5B is a photograph of the transplanted site on day 14 after transplantation of the nerve bundle implant in the sciatic nerve of the rat.

FIGS. 6A to 6C are photographs each showing a vertical cross section of a nerve bundle subjected to immunofluorescence staining with each of S100, p75NTR, and DAPI. FIG. 6D is a merged photograph of FIGS. 6A to 6C.

FIGS. 7A to 7D are photographs each showing a vertical cross section of a nerve bundle subjected to immunofluorescence staining with each of HNK-1 carbohydrate, p75NTR, MPZ, and DAPI. FIG. 7E is a merged photograph of FIGS. 7A to 7D.

Figure 8:
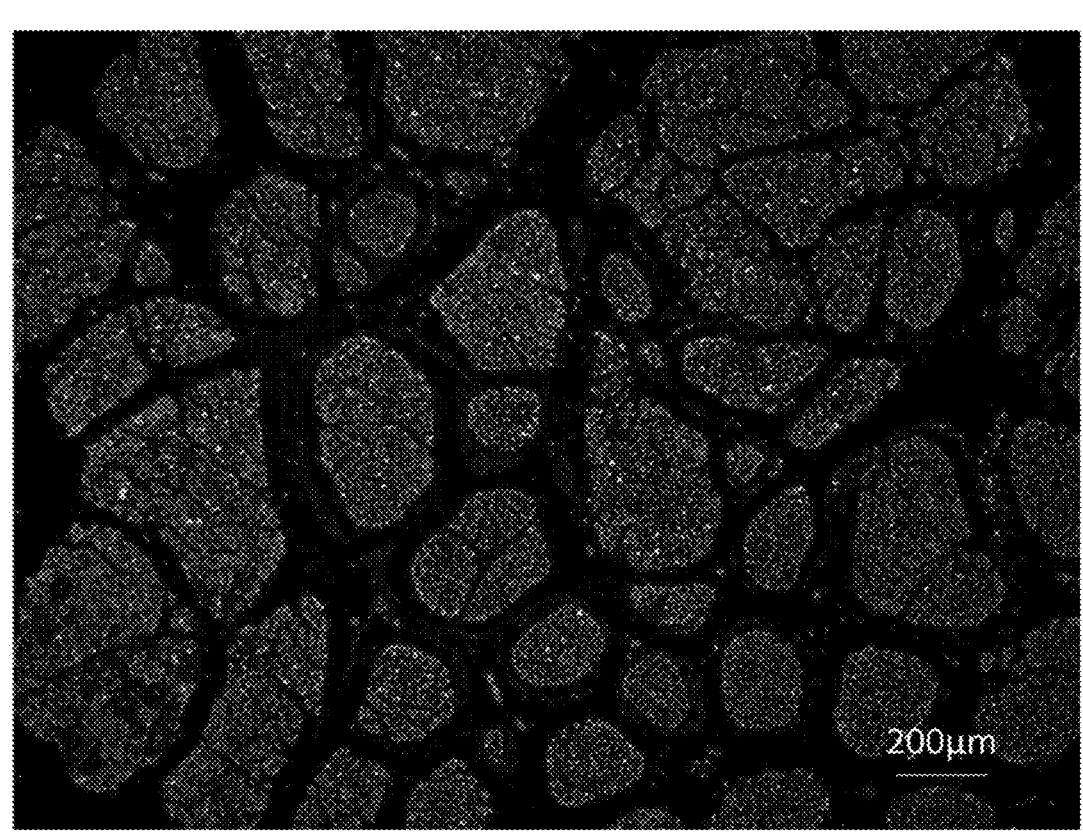

FIG. 8 is a photograph showing a cross section of a nerve bundle subjected to immunofluorescence staining with NF200 and myelin basic protein.

Figure 9A:
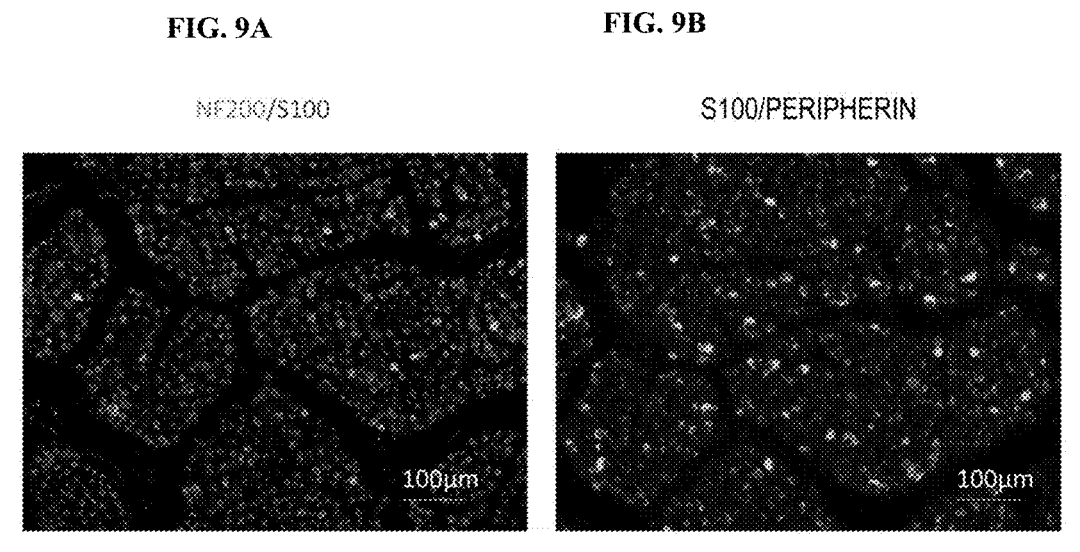

FIG. 9A is a photograph showing a cross section of a nerve bundle subjected to immunofluorescence staining with NF200 and S100. FIG. 9B is a photograph showing a cross section of a nerve bundle subjected to immunofluorescence staining with NF200 and peripherin.

Figures 10A, 10B, 10C:
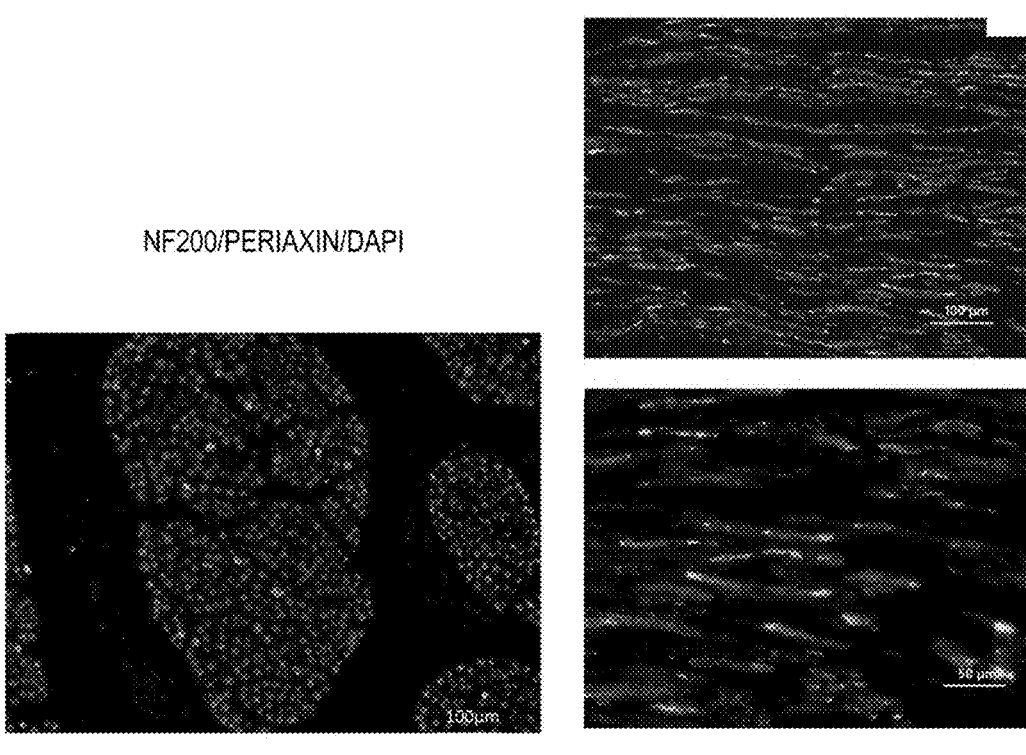

FIG. 10A is a photograph showing a cross section of a nerve bundle subjected to immunofluorescence staining with NF200 and periaxin. FIGS. 10B and 10C are photographs each showing a vertical cross section of a nerve bundle subjected to immunofluorescence staining with NF200 and periaxin.

FIGS. 11A and 11B are photographs each showing a cross section of a nerve bundle subjected to immunofluorescence staining with CD31 and PDGFRβ.

FIG. 12A is a photograph showing a cross section of a nerve bundle subjected to immunofluorescence staining with CD31 and PDGFRβ. FIG. 12B is a partially enlarged photograph of the immunofluorescence staining photograph of FIG. 12A.

Figure 13:
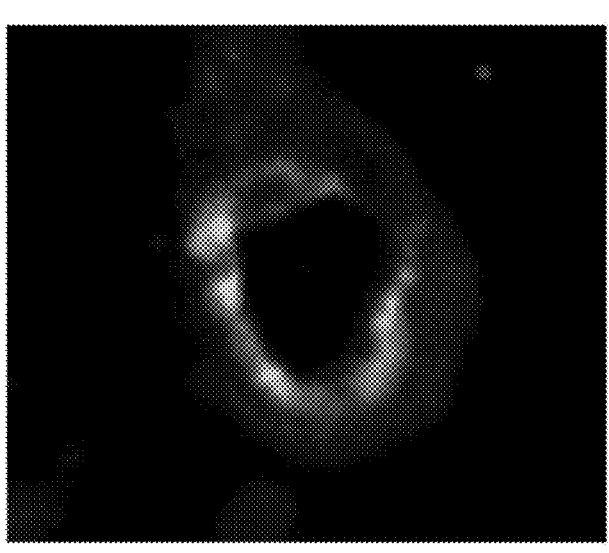

FIG. 13 is a partially enlarged photograph of a cross section of a nerve bundle subjected to immunofluorescence staining with CD31 and PDGFRβ.

FIG. 14A is a photograph of a transplanted site 12 weeks after transplantation of an autologous nerve in a rat. FIG. 14B is a photograph of a transplanted site 12 weeks after transplantation of a nerve bundle implant in a rat. FIG. 14C is a photograph of a transplanted site 12 weeks after transplantation of an artificial nerve in a rat. FIG. 14D is a photograph of a transplanted site 12 weeks after incision of a sciatic nerve of a rat.

FIG. 15A is a mathematical formula for calculating a sciatic functional index. FIG. 15B is a graph showing the sciatic functional index after transplantation (incision) in the transplanted rats and the sciatic nerve incised rat.

Figure 16:
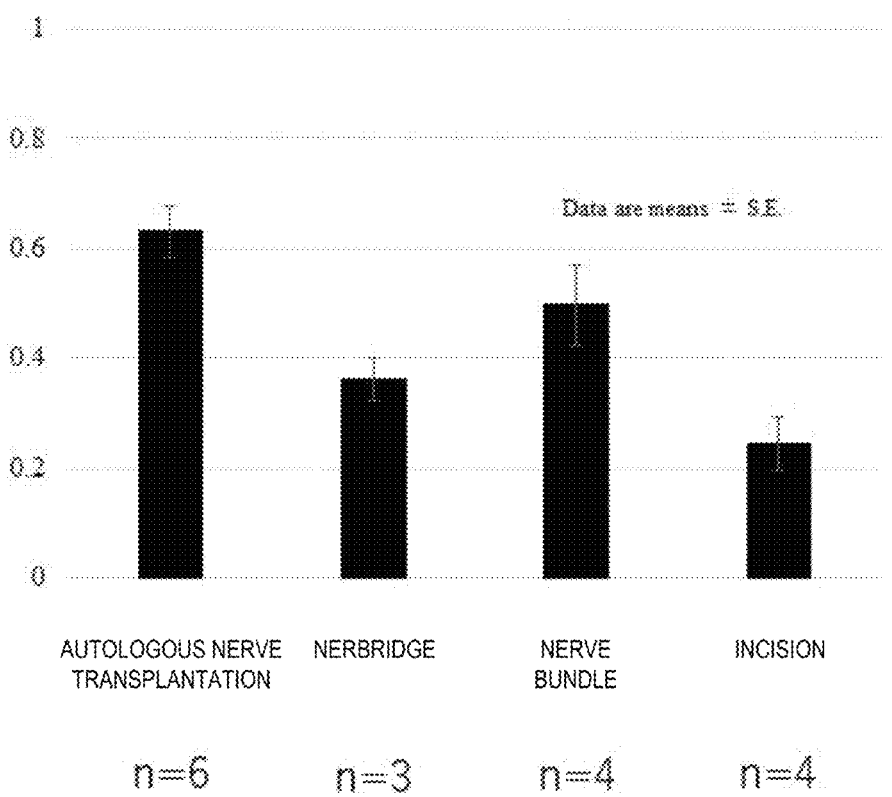

FIG. 16 is a graph showing wet weights of gastrocnemius muscles at distal ends of the transplanted sites in the transplanted rats and the sciatic nerve incised rat.

FIGS. 17A to 17D are photographs each showing a cross section of a nerve bundle subjected to immunofluorescence staining with each of STEM121, p75NTR, MPZ, and DAPI. FIG. 17E is a merged photograph of FIGS. 17A to 17D.

DETAILED DESCRIPTION OF THE INVENTION

Method of Producing Nerve Bundle

According to one aspect of the present invention, there is provided a method of producing a nerve bundle (also referred to as "production method of the present invention" hereinafter). According to the production method of the present invention, it is possible to form a nerve bundle having axons with a length and diameter sufficient for transplantation.

The method of producing a nerve bundle includes a step of cultivating a neural cell-containing cell population in the presence of feeder cells including at least one type of cells selected from vascular component cells and perivascular cells to extend axons of neural cells.

The term "neural cell-containing cell population" used herein means a population of cells containing neural cells as described below. The neural cell-containing cell population may include cells other than neural cells.

Examples of neural cells contained in the neural cell-containing population include not only cells constituting the nervous system, but also cells that may differentiate into the cells constituting the nervous system. Specific examples of neural cells to be used include neural stem cells, cells that may differentiate into neurons or glial cells, cells during differentiation into neurons or glial cells (e.g., immature neurons, immature glial cells, etc.), and differentiated mature neurons (e.g., mature neurons, mature glial cells, etc.). These neural cells may be commercially available neural cells, may be neural cells obtained by isolating neural cells from the living body and preparing the cells, or may be neural cells differentiated and induced from pluripotent stem cells such as ES cells or iPS cells. The neural cells may also be cells (autologous cells) derived from an individual to be transplanted, or may be cells (allogeneic cells) derived from an individual other than the individual to be transplanted. In a preferred embodiment, the neural cell-containing population includes neural stem cells, cells that may differentiate into neurons, cells during differentiation to neurons, and/or mature neurons. The neural cells included in the neural cell-containing cell population are not particularly limited as long as the cells do not exhibit antigenicity against the subject of transplantation of the nerve bundle of the present invention. Cells derived from any origin can be used. Examples of the origin of neural cells includes an individual that is identical to the subject of transplantation of the nerve bundle, an individual different from the subject of transplantation of the nerve bundle, and an HLA (Human Leukocyte Antigen) homo donor. Examples of the origin of neural cells include cells in which immune rejection is suppressed through modification of a human leukocyte antigen (HLA) gene by a genome editing technique, e.g., universal donor cells.

The neural cell-containing cell population may be in any form as long as the effects of the present invention are achieved, and is, for example, in the form of being suspended in a culture medium (such as αMEM, a Dulbecco's modified Eagle medium (DMEM), a mixed medium of Dulbecco's modified Eagle medium/Ham's F-12 (DMEM/F12); Ham's 10, Ham's 12 and RPMI1640 media; or various types of neuron culture media), in the form of suspension cells, or the like.

The content of neural cells in the neural cell-containing cell population is not particularly limited as long as the effects of the present invention are achieved, and the number of neural cells is, for example, from $10^3$ to $10^{10}$, preferably from $10^4$ to $10^9$, and more preferably from $10^5$ to $10^8$.

According to one embodiment of the present invention, in a nerve bundle produced by the method of the present invention, at least some, preferably all, of the neural cells in the nerve bundle have a myelin sheath including Schwann cells; a type of glial cells, in their axons. Thus, the nerve bundle produced by the method of the present invention can be used, particularly as the nerve bundle in the peripheral nervous system.

Examples of cells other than neural cells included in the neural cell-containing cell population include endothelial cells and erythrocytes. Endothelial cells capable of forming blood vessels are preferably used as the endothelial cells, and specific examples thereof include vascular endothelial cells. The cells other than neural cells included in the neural cell-containing cell population are not particularly limited as long as the cells do not exhibit antigenicity against the subject of transplantation of the nerve bundle of the present invention. Examples of the origin of cells other than neural cells includes an individual that is identical to the subject of transplantation of the nerve bundle, an individual different from the subject of transplantation of the nerve bundle, and an HLA (Human Leukocyte Antigen) homo donor. Examples of the origin of neural cells include cells in which immune rejection is suppressed through modification of a human leukocyte antigen (HLA) gene by a genome editing technique, e.g., universal donor cells.

In a case where the neural cell-containing cell population includes endothelial cells, the endothelial cells are expanded and differentiated by cultivating the neural cell-containing cell population in the presence of feeder cells, whereby a tube derived from endothelial cells is formed along the extended axons. As a result, the nerve bundle thus obtained has a tube of endothelial cells (blood vessel) that extends in the same direction as nerve fibers (axons) and adheres to nerve fibers (axons), in addition to a bundle of neural cells (nerve fibers) with extended axons.

Any of the endothelial stem cells, the cells during differentiation into the endothelial cells, and the differentiated mature endothelial cells can be used as the endothelial cells included in the neural cell-containing cell population. Further, the origin of the endothelial cells included in the neural cell-containing cell population is not particularly limited. It is preferable to use blood vessel-derived endothelial cells, it is more preferable to use blood vessel-derived endothelial cells in the pulp, gingiva, subcutaneous tissue, coelomic artery, coelomic vein, or umbilical cord, and it is even more preferable to use blood vessel-derived endothelial cells in the pulp. These endothelial cells may be commercially available endothelial cells, or may be the endothelial cells differentiated and derived from pluripotent stem cells such as ES cells or iPS cells. Further, the endothelial cells may also be autologous cells derived from an individual to be transplanted, or may be allogeneic cells derived from an individual other than the individual to be transplanted.

The content of the endothelial cells in the neural cell-containing cell population is not particularly limited as long as the effects of the present invention are achieved, and the number of endothelial cells is, for example, from $2\times10^3$ to $3\times10^{10}$, preferably from $2\times10^4$ to $3\times10^9$, and more preferably from $2\times10^5$ to $3\times10^8$. In a preferred embodiment, the number of the endothelial cells in the neuron-containing population is greater than the number of neural cells.

The neural cell-containing cell population may include a biocompatible material in addition to the aforementioned cells. The biocompatible material may be used without any particular limitation as long as the cells in the neural cell-containing cell population can adhere to the biocompatible material, and the cells in the process of cell growth and proliferation can metabolize and consume the biocompatible material. Examples of such biocompatible materials include collagen, laminin, fibronectin, gelatin, and Matrigel (trade name).

The shape of the biocompatible material is not particularly limited as long as the aforementioned effects are achieved. Examples of shapes of the biocompatible material include a bead (spherical or substantially spherical) shape, a rod shape, and a film shape.

Concerning the size of the biocompatible material with a bead shape, the diameter is, for example, from 50 to 400 μm, preferably from 100 to 300 μm, and more preferably from 100 to 200 μm.

The bead-shaped biocompatible material can be formed appropriately using a known method, and can be formed, for example, by adding a biocompatible material dropwise to an oil phase, so as to form droplets in the oil phase. Oils and fats in the oil phase are not particularly limited as long as droplets of the biocompatible material are formed. Examples of oils and fats include edible oils such as corn oil, rapeseed oil, and sesame oil; and mineral oils derived from petroleum, natural gas, and coal (mineral oils). Further, the diameter of the beads (droplets) can be appropriately adjusted by changing the dropping amount.

Preferably, the neural cells included in the neural cell-containing cell population are layered on the surface of the biocompatible material. Specifically, the layering of neural cells on the surface of the biocompatible material results in a bundle of respective neural cells with extended axons after cultivation, and this is advantageous in that a large diameter (thick) nerve bundle can be easily formed.

As the method of layering neural cells on the surface of the biocompatible material, a known method can be used. The method is, for example, a method of mixing a biocompatible material and a neural cell-containing cell population, putting the mixture into a container such as a non-adhesive petri dish, and subjecting the mixture to gyratory culture.

The amount of the neural cell-containing cell population per unit mass (g) of the biocompatible material, for example, the number of neural cells is from 200 to 1000, preferably from 300 to 800, and more preferably from 400 to 600. In the gyratory conditions, gyratory culture is performed, for example, at a speed from 30 to 60 rpm, preferably a speed from 35 to 55 rpm, more preferably a speed from 40 to 50 rpm.

When the neural cell-containing cell population includes endothelial cells, it is preferable that the endothelial cells included in the neural cell-containing cell population are layered on the surface of the biocompatible material. Specifically, the layering of endothelial cells on the surface of the biocompatible material results in the contact and fusion of a plurality of biocompatible materials with layers of endothelial cells derived from endothelial cells included in the neural cell-containing cell population in the cultivating process. As a result, it is possible to form a tube of endothelial cells which has a surface comprised of endothelial cells and includes the biocompatible material therein. Then, the endothelial cells constituting the tube surface uptake, metabolize, and consume the biocompatible material in the tube in the process of endothelial cell growth and proliferation, resulting in the formation of a hollow tube of endothelial cells. It is advantageous that the formed tube of endothelial cells can serve as a tube (blood vessel) that supplies oxygen, nutrients, and the like to the neural cells in the nerve bundle to be formed, thereby preventing the necrosis of the nerve bundle. The method of layering endothelial cells on the surface of the biocompatible material may be the same method as the aforementioned method of layering neural cells on the surface of the biocompatible material.

In order to achieve the advantages of layering neural cells and endothelial cells on the surface of the biocompatible material, it is preferable that the neural cells and the endothelial cells are each layered on the surfaces of different biocompatible materials. Specifically, it is preferable that the neural cells are layered on the surface of a biocompatible material, and the endothelial cells are layered on the surface of another biocompatible material.

The biocompatible material may be mixed, in advance, with a substance that promotes the growth and proliferation of neural cells (neural cell growth factor), such as a nerve growth factor (NGF), a fibroblast growth factor-β (β-FGF), a vascular endothelial growth factor (VEGF), a hepatocyte growth factor (HGF), or a trophic growth factor. The biocompatible material includes a neural cell growth factor, so that it is possible to more efficiently promote the growth of neural cells present on the surface of the biocompatible material.

The proportion of the neural cell growth factor mixed with the biocompatible material can be appropriately set depending on the size of the nerve bundle to be formed, and the proportion is, for example, from 1 to 1000 ng/mg, from 5 to 750 ng/mg, and from 10 to 500 ng/mg, relative to the total mass of the biocompatible material.

The neural cell growth factors may be used singly, or may be further mixed with ganglioside 3 (GD3) as a type of carbohydrate. The amount of GD3 mixed with the biocompatible material is not particularly limited, and is, for example, from 10 to 100 ng/mg, from 10 to 75 ng/mg, and from 10 to 50 ng/mg. In the case of adding the biocompatible material and the neural cell growth factors to a recess separately, the neural cell growth factors (a neural cell growth factor and GD3 when GD3 is used) are put into the recess and then the neural cells are put into the recess, thereby promoting the extension of the axons.

When the neural cell-containing cell population include endothelial cells, the biocompatible material may be mixed, in advance, with a substance that promotes the growth and proliferation of endothelial cells (endothelial cell growth factor), such as a vascular endothelial growth factor (VEGF). The biocompatible material includes the endothelial cell growth factor, so that it is possible to more efficiently promote the growth of endothelial cells present on the surface of the biocompatible material.

The proportion of the endothelial cell growth factor mixed with the biocompatible material can be appropriately set depending on the size of the nerve bundle produced, and the proportion is, for example, from 10 to 300 ng/ml, from 20 to 200 ng/ml, and from 30 to 100 ng/ml, relative to the total mass of the biocompatible material.

When the biocompatible material and endothelial cells are separately added to the recess, the biocompatible material and endothelial cells are preferably added to the recess so that the endothelial cells adhere to the surface of the biocompatible material. The addition of the biocompatible material and endothelial cells in this manner can further promote the formation of blood vessels with lumens.

When the neural cell-containing cell population includes endothelial cells, the biocompatible material may be mixed with erythrocytes in advance. The biocompatible material includes erythrocytes so that erythrocytes can be present within a hollow tube of endothelial cells formed in the process of cultivating the neural cell-containing cell population. As a result, a complete hollow tube of endothelial cells can be formed. Then, in the formed nerve bundle, oxygen is delivered to the neural cells by erythrocytes and the culture solution via the formed hollow tube of endothelial cells, so that it is possible to prevent the necrosis of the nerve bundle.

The amount of erythrocytes mixed with the biocompatible material can be set as appropriate depending on the size of the nerve bundle to be formed. The amount is, for example, from 2 to 20 mass %, preferably from 3 to 10 mass %, and more preferably from 4 to 7 mass %, relative to the amount of the biocompatible material.

The term "feeder cells" used herein refers to cells that produce and secrete substances that induce or retain the survival, proliferation, and differentiation of neural cells and optionally endothelial cells, and promotes the extension and enlargement of neural cells. The substances produced and secreted by the feeder cells are not particularly limited as long as the substances have the aforementioned functions. Examples of such substances include a nerve growth factor (NGF), a vascular endothelial growth factor (VEGF), a hepatocyte growth factor (HGF), a fibroblast growth factor (FGF-β), a trophic factor, a growth hormone-like substance, and IGF-1.

Feeder cells include cells that produce and secrete the substances as aforementioned. Specifically, the feeder cells include at least one type of cells selected from vascular component cells constituting blood vessels, perivascular cells around the blood vessels, oligodendrocytes, and Schwann cells.

Vascular component cells are not particularly limited as long as the effects of the present invention are achieved. Examples of vascular component cells include pericytes (e.g., vascular pericytes) and endothelial cells (e.g., vascular endothelial cells). Further, examples of perivascular cells include fibroblasts (e.g., perivascular fibroblasts) and smooth muscle cells (e.g., vascular smooth muscle cells).

Both oligodendrocytes and Schwann cells are a type of glial cells that constitute the myelin sheath in the nervous system. Oligodendrocytes constitute the myelin sheath in the central nervous system and are also referred to as oligodendroglial cells. Schwann cells also constitute the myelin sheath in the peripheral nervous system.

The method of producing a nerve bundle is not particularly limited as long as the method includes a step of cultivating a neural cell-containing cell population in the presence of feeder cells including at least one type of cells selected from vascular component cells and perivascular cells to extend axons of neural cells. The step can be performed, for example, as in steps (a) to (c) below.

Step (a)

This step prepares a substrate including at least one recess and a channel portion connected to the recess, the channel portion being covered with feeder cells.

The material of the substrate is not particularly limited as long as the effects of the present invention are achieved, and examples of materials of the substrate include dimethylpolysiloxane, polystyrene, and polypropylene.

The shape and dimensions of the substrate can be set as appropriate as long as the effects of the invention of the present application are achieved. The substrate preferably has at least one plane, and the shape is, for example, a rectangular parallelepiped, a cube, or a cylinder, and is preferably a rectangular parallelepiped.

The dimensions of the substrate are not particularly limited as long as the substrate includes at least one recess and a channel portion. For example, when the shape is a rectangular parallelepiped, the vertical and horizontal lengths of the rectangular parallelepiped substrate are from 5 to 20 cm, from 5 to 15 cm, from 5 to 10 cm, and the height (depth) of the substrate is from 1 to 10 cm, from 1 to 5 cm, and from 1 to 3 cm.

The substrate includes at least one recess for accommodating a neural cell-containing cell population. When the substrate is provided with a plurality of recesses, the arrangement of the plurality of recesses is not particularly limited as long as the effects of the present invention are achieved. Preferably, the plurality of recesses is present on the same plane of the substrate. For example, the substrate includes two recesses, and the two recesses are present on the same plane of the substrate.

The shape and dimensions of a recess can be set as appropriate as long as the effects of the present invention are achieved. Examples of shapes of the recess include a cylindrical shape, a rectangular parallelepiped shape, a cubic shape, and a hemispherical shape.

When the shape of the recess is cylindrical, in the dimensions of the cylindrical recess, the diameter is, for example, from 1 to 15 mm, preferably from 1 to 10 mm, and more preferably from 1 to 7 mm, and the height (depth) is from 2 to 8 mm, preferably from 3 to 7 mm, and more preferably from 4 to 6 mm. When the substrate includes a plurality of recesses, the shapes and/or dimensions of the recesses may be identical to or different from each other.

The substrate includes a channel portion connected to a recess, and the channel portion is covered with feeder cells. The channel portion may be covered with fibroblasts before covered with the feeder cells. In a case where the channel portion is covered with fibroblasts, the channel portion is preferably first covered with the fibroblasts, and then the feeder cells are applied onto the fibroblast-covered channel portion. The arrangement of the channel portion is not particularly limited as long as the effects of the present invention are achieved, and the channel portion and the recess are present on the same plane. Further, when the substrate includes a plurality of recesses, each of the recesses is connected to the channel portion, and the plurality of recesses is preferably connected through the channel portion. For example, the substrate includes two recesses on the same plane, and the two recesses are connected through the channel portion present on the same plane as the two recesses.

The shape (cross-sectional shape) and the dimensions (length and depth) of the channel portion can be set as appropriate as long as the effects of the present invention are achieved. Examples of shapes of the channel portion include a concave shape, a V-shape, a U-shape, and an Ω-type shape.

The length of the channel portion (distance from the recess) is, for example, from 3 to 50 mm, preferably from 15 to 40 mm, and more preferably from 20 to 30 mm. The depth of the channel is, for example, from 50 to 300 μm, preferably from 75 to 250 μm, and more preferably from 100 to 200 μm. The width of the channel is, for example, from 50 to 300 μm, preferably from 75 to 250 μm, and more preferably from 100 to 200 μm. When the substrate includes a plurality of recesses, the length of the channel portion refers to a length (distance) between the recesses.

Step (b)

In this step, the neural cell-containing cell population is added to the recess. In a preferred embodiment, the neural cell-containing cell population in a state of being layered on the biocompatible material, preferably the surface of beads such as collagen beads, is added to the recess. When the neural cell-containing cell population includes endothelial cells, the neurons in the neural cell-containing cell population are added to the recess in a state in which the neurons are layered on a biocompatible material, preferably the surface of beads such as collagen beads, and the endothelial cells in the neural cell-containing cell population are added to the recess in a state in which the endothelial cells are layered on different biocompatible materials, preferably the surface of beads such as collagen beads. The amount of the neural cell-containing cell population to be added to the recess is not particularly limited as long as the effects of the present invention are achieved, and the number of neural cells is, for example, from $10^3$ to $10^{10}$, preferably from $10^4$ to $10^9$, and more preferably from $10^5$ to $10^8$. Further, when the neural cell-containing cell population includes endothelial cells, the amount of endothelial cells to be added to the recess; the ratio of the number of neural cells to the number of endothelial cells (number of neural cells: number of endothelial cells) is, for example, from 1:1 to 1:10, from 1:2 to 1:7, and from 1:3 to 1:5.

Step (c)

In this step, axons of neural cells are extended along the channel portion of the substrate by adding a culture solution to the recess and the channel portion of the substrate and cultivating the neural cell-containing cell population.

The culture solution to be added is not particularly limited as long as it is a culture solution that is normally used in cultivating neural cells. Examples of culture solutions include basal media such as neuron culture media; DMEM and RPMI1640 media; EMEM, Ham's 10 and Ham's 12 media; and a modified basal medium DMEM/F12. Various amino acids such as L-glutamine and L-alanine, additives such as fetal bovine serum (FBS), albumin, and the like may be added to these culture media. In the case of adding FBS to each culture medium, the concentration in each culture medium is, for example, from 5 to 20 mass %, from 7 to 15 mass %, and from 10 to 15 mass %. In the method of adding a culture solution, the culture solution may be added to each of the recess and the channel portion, or the substrate is immersed in a container that has filled with the culture solution in advance, and the culture solution may be supplied to each of the recess and the channel portion.

Culture conditions are not particularly limited as long as the cells contained in the neural cell-containing cell population grow and proliferate. Examples of culture conditions include static culture at a temperature of 35 to 38° C. and a $CO_2$ concentration from 3 to 5% for a culture time of 20 to 24 hours. Depending on the degree of extension of the axons of neural cells, the static culture may be combined with the reflux culture. Reflux culture conditions can be set, for example, as follows: a temperature of 35 to 38° C.; a $CO_2$ concentration from 3 to 5%; a reflux rate from 1 to 10 ml/hour (preferably a reflux rate from 2 to 5 ml/hour); and a culture time of 72 hours to 60 days.

Nerve Bundle Produced by Production Method of Present Invention

According to one aspect of the present invention, there is provided a nerve bundle produced by the method described above. The nerve bundle produced by the production method of the present invention is subjected to appropriate processing as necessary, and the processed nerve bundle can be used as an implant, particularly a nerve regeneration implant.

A plurality of nerve bundles is combined as necessary, and the resultant bundle can be used as a bundle of nerve bundles. The bundle of nerve bundles can be formed by rolling (covering) the plurality of nerve bundles with a biocompatible material sheet prepared in advance. The biocompatible material sheet is not particularly limited as long as the effects of the present invention are achieved. Examples of biocompatible material sheets include a fibroblast sheet, a collagen fiber network sheet, and an elastic fiber network sheet.

According to one embodiment, a plurality of nerve bundles is arranged on a fibroblast sheet prepared in advance, and the plurality of nerve bundles is rolled into a roll (nori-maki; vinegared rice rolled in dried layer) with the fibroblast sheet to form a bundle of nerve bundles. The thickness (diameter) of the bundle of nerve bundles can be optionally changed according to the number of nerve bundles arranged on the fibroblast sheet. As described above, when the nerve bundles are rolled with the fibroblast sheet, the ends of the fibroblast sheet are sutured to the nerve lesion site (nerve stump) to be transplanted, and thus the nerve bundles can be easily transplanted.

The nerve bundles can be used as an implant (nerve regeneration implant) as a substitute for damaged nerves. The subject of transplantation is not particularly limited. For example, the nerve bundle can be transplanted into the central nervous system, the peripheral nervous system, or the like, and is preferably transplanted into the peripheral nervous system.

Nerve bundles can also be formed using cells (autologous cells) derived from an individual to be transplanted, and can also be formed using cells (allogeneic cells) derived from an individual other than the individual to be transplanted. Therefore, the formation of the nerve bundles using autologous cells makes is possible to transplant (autotransplant) the nerve bundles to an individual from which the cells as the material of the nerve bundles are derived, while causing little rejection.

Method of Extending Axons of Neural Cells

According to one aspect of the invention, there is provided a method of extending axons of neural cells (hereinafter, also referred to as "method of the present invention"). The method of the present invention allows axons of neural cells to efficiently extend. Further, the method of the present invention can efficiently increase the diameter of axons of nerves.

The method of the present invention includes a step of cultivating a neural cell-containing cell population in the presence of feeder cells including at least one type of cells selected from vascular component cells and perivascular cells to extend axons of neural cells.

In the method of the present invention, the neural cell-containing cell population and feeder cells can be the same as described in the aforementioned method of producing a nerve bundle.

In the method of the present invention, the specific conditions of the step of cultivating a neural cell-containing cell population in the presence of feeder cells including at least one type of cells selected from vascular component cells or perivascular cells to extend axons of neural cells can be the same as described in the method of producing a nerve bundle.

Nerve Bundle

According to one aspect of the present invention, there is provided a nerve bundle including: neural cells with extended axons; and a tube of endothelial cells present along the axons, in which the nerve bundle includes at least one type of cells selected from HNK-1 carbohydrate-expressing cells and p75NTR-expressing cells (hereinafter, also referred to as "nerve bundle of the present invention").

The HNK-1 (human natural killer-1) carbohydrate, also referred to as CD57, has been found as a carbohydrate antigen expressed on human natural killer cells recognized by the monoclonal antibody HNK-1. The HNK-1 carbohydrate is known to be expressed in the nervous system of many vertebrates, including humans.

The p75NTR (p75 neurotrophin receptor) is also referred to as a low affinity neurotrophic factor receptor and is a receptor for a 75 kDa single-pass transmembrane neurotrophic factor receptor belonging to the tumor necrosis factor (TNF) receptor superfamily.

Both the HNK-1 carbohydrate and the p75NTR are known as markers for neural crest stem cells that are primarily expressed at the early stage of development in which neural crest cells are separated from the dorsal neural tube in vertebrates (particularly humans). Hence, the HNK-1 carbohydrate and the p75NTR are expressed in the immature nervous system of vertebrates in the embryonic stage, whereas both the HNK-1 carbohydrate and the p75NTR are very weakly expressed or not expressed in the nervous system of vertebrates after embryonic development. Therefore, both the HNK-1 carbohydrate and the p75NTR are very weakly expressed or not expressed in the mature nervous system of normal adult vertebrates.

In general, it is very difficult and substantially impossible to obtain a nerve bundle from the immature nervous system of the embryo at the early stage of development, and it is known that there is no nerve bundle that includes cells expressing HNK-1 carbohydrate and/or p75NTR. Consequently, the nerve bundle of the present invention is said to be very specific in that it substantially expresses HNK-1 carbohydrate and/or p75NTR.

In a preferred embodiment, the nerve bundle of the present invention includes HNK-1 carbohydrate-expressing cells and p75NTR-expressing cells. The HNK-1 carbohydrate-expressing cells and the p75NTR-expressing cells may be identical or different. In other words, both the HNK-1 carbohydrate and the p75NTR may be expressed in one cell, and the HNK-1 carbohydrate and the p75NTR may be each expressed in different cells.

Concerning the HNK-1 carbohydrate and the p75NTR, "HNK-1 carbohydrate-expressing cells" and "p75NTR-expressing cells" refer to cells that substantially express HNK-1 carbohydrate and cells that substantially express p75NTR, respectively. Here, the phrases "substantially express" and "substantially expressed", and the like refer to a state in which gene transcription products or translation products are produced in cells. Specifically, the p75NTR is bound to a nerve growth factor (NGF), a brain-derived neurotrophic factor (BDNF), neurotrophin-3 (NT-3), neurotrophin-4/5 (NT-4/5), or like to control the extension of axons of neurons. Further, the HNK-1 carbohydrate also has an increased expression during the stage of nerve development and is involved in neural circuit formation. Both the p75NTR and the HNK-1 carbohydrate are markers for neural crest stem cells and are known to be very weakly expressed or not expressed in the mature nervous system. Accordingly, it can be said that the nerve bundle of the present invention in which these markers are expressed are different from the known nerve bundles and implants obtained by using normal peripheral nerves or neurons in the mature nervous system.

In the present invention, expressions of HNK-1 carbohydrate and p75NTR in cells can be confirmed by detecting expressions of the genes by immunostaining with an antibody against HNK-1 carbohydrate and an antibody against p75NTR.

In a preferred embodiment, HNK-1 carbohydrate-expressing cells and/or p75NTR-expressing cells are neural cells. In other words, in a preferred embodiment, the nerve bundle of the present invention includes neural cells expressing HNK-1 carbohydrate and/or p75NTR.

In a preferred embodiment, the nerve bundle of the present invention includes at least one type of cells selected from the group consisting of cells that express NS200 (NS200-expressing cells), cells that express peripherin (peripherin-expressing cells), cells that express myelin basic protein (myelin basic protein-expressing cells), cells that express S100 (S100-expressing cells), cells that express MPZ (MPZ-expressing cells), cells that express periaxin (periaxin-expressing cells), cells that express CD31 (CD31-expressing cells), and cells that express PDGFRβ (PDGFRβ-expressing cells). The cells expressing each of the above genes may be identical or different. In other words, this embodiment encompasses a case where two or more of the genes described above are expressed in one cell. For example, NS200-expressing cells may be cells that express only NS200 of the genes described above, and may be cells that express any of the genes described above in addition to NS200.

In a particularly preferred embodiment, the nerve bundle of the present invention includes all the following cells: NS200-expressing cells; peripherin-expressing cells; myelin basic protein-expressing cells; S100-expressing cells; MPZ-expressing cells; periaxin-expressing cells; CD31-expressing cells; and PDGFR-expressing cells.

All the genes; NF200, peripherin, myelin basic protein, S100, MPZ, and periaxin are known as expression markers for nervous system. Specifically, NF200 (Neurofilament 200) and peripherin each are known as a neuronal marker for myelinated nerves. Here, S100 is also known as a marker for Schwann cells. The myelin basic protein, S100, MPZ (Myelin protein zero) and periaxin each are known as a marker for myelin sheath.

Meanwhile, both the CD31 gene and the PDGFRβ gene are known as expression markers for vascular system. Specifically, the CD31 is known as a marker for vascular endothelial cells. The platelet-derived growth factor receptor β (PDGFRβ) is also known as a marker for vascular pericytes and fibroblasts.

The presence or absence of expressions of the above genes can be confirmed by the same method as in the method of confirming the presence or absence of expressions of HNK-1 carbohydrate and p75NTR as aforementioned.

The nerve bundle of the present invention has a tube of endothelial cells that is present along the axons of the neural cells. At least some of the endothelial cells constituting the tube are preferably blood vessel-derived endothelial cells, more preferably blood vessel-derived endothelial cells in the pulp, gingiva, subcutaneous tissue, coelomic artery, coelomic vein, or umbilical cord, and still more preferably blood vessel-derived endothelial cells in the pulp. Further, the endothelial cells may also be autologous cells derived from an individual to be transplanted with the nerve bundle, or may be allogeneic cells derived from an individual other than the individual to be transplanted. It is advantageous that the tube of endothelial cells has the advantage that can serve as a tube (blood vessel) that supplies oxygen, nutrients, and the like to the neural cells in the nerve bundle, thereby preventing the necrosis of the nerve bundle.

In a preferred embodiment, the tube of endothelial cells as aforementioned further includes pericytes. The tube of endothelial cells further includes pericytes, specifically the tube of endothelial cells is lined with pericytes, as a result of which the tube of endothelial cells is reinforced. In a case where the nerve bundle of the present invention is responsible for the vascular role of endothelial cells, the reinforced tube of endothelial cells allows blood to flow stably into the tube of endothelial cells.

In a preferred embodiment, the nerve bundle of the present invention has a cell layer including at least one type of cell selected from fibroblasts and pericytes that cover, along the axons of the neural cells, at least some of, or preferably all of, the axons. In a particularly preferred embodiment, the nerve bundle of the present invention has the aforementioned tube of endothelial cells in the cell layer.

The nerve bundle of the present invention can be used as an implant, particularly a nerve regeneration implant as a substitute for damaged nerves. The subject of transplantation of the nerve bundle is not particularly limited. For example, the nerve bundle can be transplanted in the central nervous system, the peripheral nervous system, or the like, and is preferably transplanted in the peripheral nervous system.

EXAMPLES

Hereinafter, the present invention will be specifically described with reference to examples, but the present invention is not limited to these examples.

Example 1: Formation of Neural Cell-Containing Cell Population

A neural cell-containing cell population used in this example was formed according to the following procedure.

Oral mesenchymal cells harvested from the human pulp, gingival epithelial tissue basal layer, and oral epithelial tissue basal layer were seeded onto a cell adhesive petri dish (IWAKI & CO., LTD.) and passaged till 3 to 7 passages at 37° C. and a $CO_2$ concentration of 4.5 to 5.5% using a mixed medium of Dulbecco's modified Eagle medium/Ham's F12 (DMEM/F12). The cells were separated with a trypsin-EDTA solution, the separated cells were seeded thinly (in a small number) onto a new petri dish, and large colonies with high growth potential were subjected to colonial cloning to obtain pulp-derived mesenchymal stem cells. The resultant stem cells were cultivated in a culture medium obtained by adding 10 ng/ml of epidermal growth factor (EGF) and 10 ng/ml of fibroblast growth factor-β (β-FGF) to a neural induction medium (differentiation induction medium described in Takahashi et al., Human Cell, Vol. 30, Issue 2, pp 60-71) at 37° C. and a $CO_2$ concentration of 4.5 to 5.5%, and differentiation induction was performed on the resultant culture to form a neural cell-containing cell population. Analyses by immunostaining and RT-PCR confirmed that neural stem cells, immature neurons, immature glial cells, mature neurons, and mature glial cells were included as the cells after differentiation induction. As a result of immunostaining with tyrosine hydroxylase antibodies, it was also confirmed that dopamine cells were included as the cells after differentiation induction.

Example 2: Formation of Endothelial Cells

Endothelial cells used in this example were formed according to the following procedure.

The vascularized tissue harvested from the human oral cavity was treated with a digestive enzyme to separate the cells, and primary culture was performed on the separated cells. Colonies of morphologically identifiable endothelial cells were separated by colonial cloning, and the separated colonies were expanded to obtain endothelial cells. Alternatively, primary cultured cells were seeded onto a Matrigel-coated petri dish, the cells were cultured in a culture solution containing VEGF (from 10 to 50 ng/ml) to separate structures forming the lumen, and the cells constituting the structures were expanded to obtain endothelial cells.

Example 3: Formation of Neural Cell Beads

Neural cell beads used in this example were formed according to the following procedure.

To an atelocollagen solution (available from KOKEN CO., LTD.), a 10-fold concentrated Dulbecco's modified Eagle's medium/Ham's F-12 (DMEM/F12) mixed medium was added so as to be 10 mass %, and the resultant mixture was stirred and mixed to obtain an atelocollagen mixed liquid. A biocompatible material (collagen beads) was formed by adding the obtained atelocollagen mixed liquid dropwise to corn oil so that the diameter of particles (beads) of the atelocollagen was 200 μm. The obtained collagen beads were mixed with the neural cell-containing cell population formed in Example 1 at a mass ratio of 1:500. After mixing, the resultant mixture was put into a non-adhesive petri dish (manufactured by IWAKI & CO., LTD.) and cultivated at a gyratory speed from 40 to 60 rpm, and the neural cell-containing cell population was layered on the surface of the collagen beads to form neural cell beads.

Example 4: Formation of Endothelial Cell Beads

Endothelial cell beads used in this example were formed according to the following procedure.

To an atelocollagen solution (available from KOKEN CO., LTD.), an 8- to 10-fold concentrated RPMI1640 medium was added so as to be 10 mass %. Further, a vascular endothelial growth factor (VEGF) (available from Sigma-Aldrich Co. LLC) was added so as to be 50 ng/ml, erythrocytes were added so as to be 5 mass %, and the resultant mixture was stirred and mixed to obtain an atelocollagen mixed liquid. A biocompatible material (collagen beads) was formed by adding the obtained atelocollagen mixed liquid dropwise to corn oil so that the diameter of particles (beads) of the atelocollagen was 100 μm. The obtained collagen beads were mixed with the endothelial cells formed in Example 2 at a mass ratio of 1:500. After mixing, the resultant mixture was put into a non-adhesive petri dish (IWAKI & CO., LTD.) and cultivated at a gyratory speed from 40 to 60 rpm, and endothelial cells were layered on the surface of the collagen beads to form endothelial cell beads.

Example 5: Production of Nerve Bundle Forming Device

A device for forming a nerve bundle was made according to the following procedure.

Figure 1:
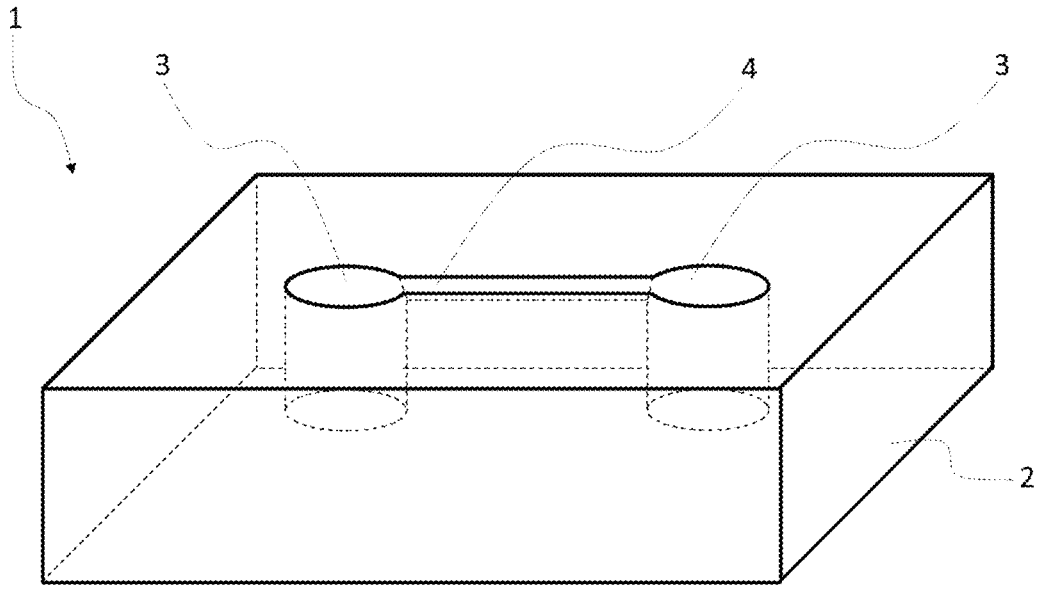
FIG. 1 is a schematic view of a device for forming a nerve bundle.

Two recesses having a diameter of 5 mm and a depth of 5 mm were formed at an interval of 3 cm on a surface of a dimethylpolysiloxane substrate (5 cm in length, 5 cm in width, and 1 cm in thickness). Further, a linear channel portion (having a width of 150 μm and a depth of 150 μm) for connecting the two recesses was formed between the two recesses, and the device for forming a nerve bundle was produced. FIG. 1 shows a schematic view of the produced device.

Example 6: Formation of Nerve Bundles

Prior to the formation of nerve bundles, feeder cells suitable for extending axons of neural cells were investigated by the procedure below.

Figure 2:
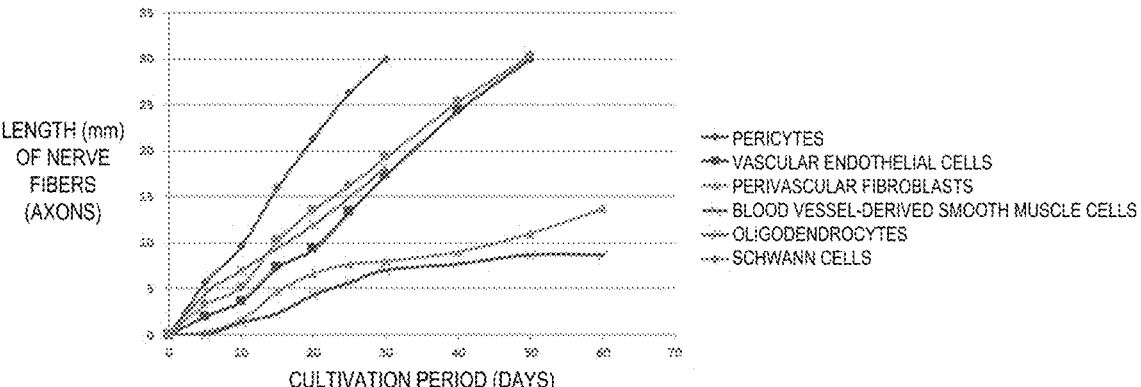
FIG. 2 is a graph showing a relationship between the cultivation period and the length of nerve fibers (axons) in the case of using various cells as feeder cells.

Four devices formed in Example 5 were prepared, and vascular component cells (vascular pericytes, vascular endothelial cells, and blood vessel-derived smooth muscle cells), perivascular cells (perivascular fibroblasts), oligodendrocytes or Schwann cells as feeder cells were seeded onto the channel portion of each of the devices. Thereafter, each of the devices was placed in a culture vessel, and DMEM/F12 supplemented with 15 mass % fetal bovine serum (FBS) was added to the culture vessel. The culture vessel was left to stand still in a $CO_2$ incubator (at a temperature 37° C. and a $CO_2$ concentration of 4.7%), and the cells in the channel portion of each of the devices were cultivated to form a monolayer of each of the cells in the channel portion. Then, the neural cell beads formed in Example 3 and the endothelial cell beads formed in Example 4 were mixed at a mass ratio of 3:1, and the mixture was added to each of two recesses of each of the devices using a micropipette. The DMEM/F12 medium was added to each of the recesses, and each of the devices was left to stand still in a $CO_2$ incubator (at a temperature 37° C. and a $CO_2$ concentration of 4.7%) for cultivation for 20 hours. Each of the devices was then placed in a chamber (6 cm in length×6 cm in width×2 cm in thickness) and incubated under reflux (at a flow rate of 2 ml/min, a temperature of 37° C., and a $CO_2$ concentration of 4.7%) for 72 to 168 hours so as to cause axons of neural cells to extend on each of the cell layers in the channel portion. Then, a relationship between the cultivation period and the length of the nerve bundles was investigated. The results are shown in FIG. 2. Although not shown in FIG. 2, when cultivation was performed using vascular pericytes, vascular endothelial cells, perivascular fibroblasts, blood vessel-derived smooth muscle cells, oligodendrocytes or Schwann cells as feeder cells, on day 30 after the start of cultivation, the diameter of axons in each case were approximately from 100 to 150 µm, approximately from 50 to 80 µm, approximately from 20 to 30 µm, and approximately from 10 to 20 µm. Meanwhile, when feeder cells were not used, almost of the axons of neural cells were not enlarged, and the length on day 30 after the start of cultivation was approximately from 5 to 10 µm and the diameter was approximately from 5 to 10 µm.

The results of FIG. 2 showed that the axons of neural cells were efficiently extended when vascular component cells, perivascular cells, oligodendrocytes or Schwann cells were used as feeder cells. Particularly, it was shown that when vascular pericytes or vascular endothelial cells, i.e., vascular component cells, were used as feeder cells, the axons of neural cells were extended very efficiently.

A nerve bundle was formed by the following procedure using vascular pericytes as feeder cells.

Figure 3A:
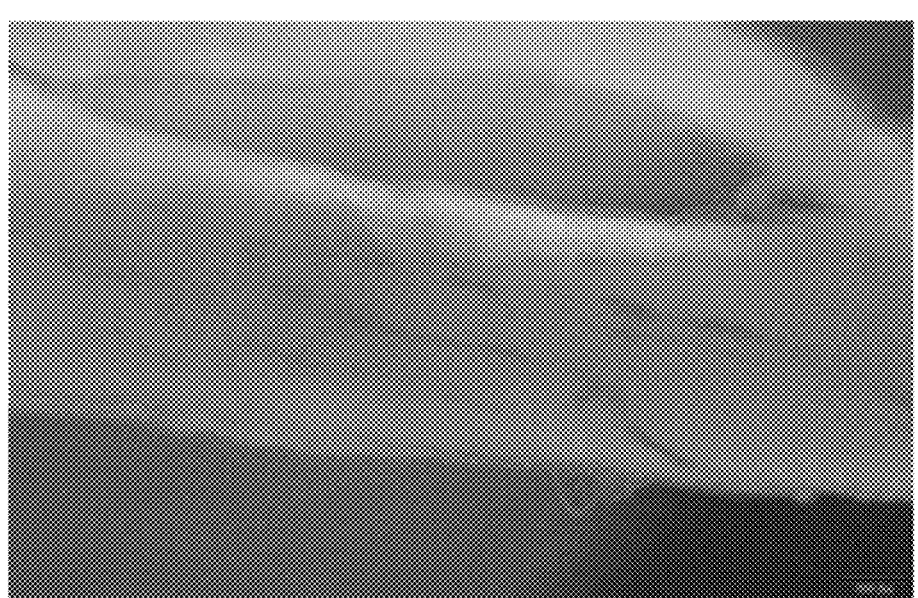
FIG. 3A is an actual micrograph of a formed nerve bundle.
Figure 3B:
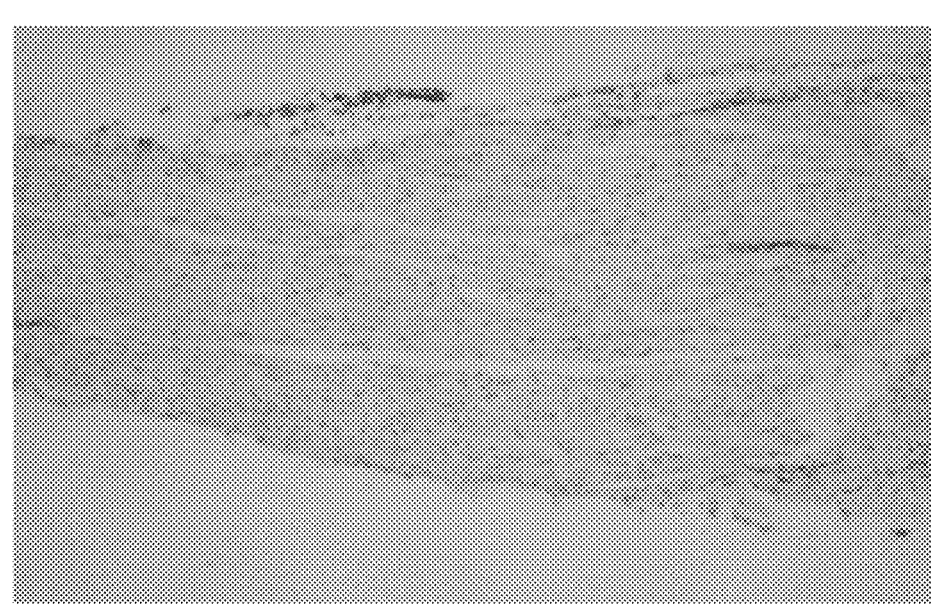
FIG. 3B is an image of Hematoxylin-eosin (HE) staining of the formed nerve bundle (image of a vertical cross-section).

Fibroblasts were seeded onto the channel portion of the device formed in Example 5 to form a monolayer of fibroblasts. The human-derived vascular pericytes were then seeded onto fibroblasts to form a monolayer to multilayer of vascular pericytes. Thereafter, the device was placed in a culture vessel, and DMEM/F12 supplemented with 15 mass % fetal bovine serum (FBS) was added to the culture vessel. The culture vessel was left to stand still in a $CO_2$ incubator (at a temperature of 37° C. and a $CO_2$ concentration of 4.7%) to cultivate fibroblasts and vascular pericytes in the channel portion of the device, thereby forming a monolayer of fibroblasts and a monolayer of vascular pericytes adhered onto the fibroblast layer in the channel portion. Then, the neural cell beads formed in Example 3 and the endothelial cell beads formed in Example 4 were mixed at a mass ratio of 3:1, and the mixture was added to each of two recesses of the device using a micropipette. The DMEM/F12 medium was added to each of the recesses and the device was left to stand still in a $CO_2$ incubator (at a temperature 37° C. and a $CO_2$ concentration of 4.7%) for incubation for 20 hours. Then, the device was placed in a chamber (6 cm in length×6 cm in width×2 cm in thickness) and incubated under reflux (at a flow rate of 2 ml/min, a temperature of 37° C., and a $CO_2$ concentration of 4.7%) for 30 days so as to cause axons of neural cells to extend on the fibroblast layer and the vascular pericyte layer in the channel portion, thereby obtaining a bundle of neural cells (nerve fibers) with extended axons (nerve bundle of the present invention). Here, the nerve bundle thus obtained had a tube of endothelial cells (blood vessel) extended in the same direction as nerve fibers (axons) and adhered to nerve fibers (axons), in addition to the bundle of neural cells (nerve fibers) with extended axons. Further, the nerve bundle had a length of about 3 cm and a diameter of about 100 to 150 µm. Furthermore, the fibroblasts constituting the fibroblast layer grew and proliferated to form a sheet of fibroblasts in the channel portion. Micrographs and immunostaining images of the resulting nerve bundle are shown in FIG. 3 (A: stereomicroscope image, B: hematoxylin-eosin (HE) stained (vertical cross section image)). In FIGS. 3A and 3B, a portion along the nerve bundle is a tube of endothelial cells (blood vessel). Immunostaining images of the resulting nerve bundle are also shown in FIG. 4. In FIGS. 4A and 4B, a white or gray linear portion along the nerve bundle is a tube of endothelial cells (blood vessel). Hence, the nerve bundle formed by the method of this example has a tube of endothelial cells (blood vessel) present along axons, in addition to the neural cells with extended axons.

Next, the nerve bundle formed in the channel portion was covered by rolling with the sheet of fibroblasts formed in the channel portion. A plurality of nerve bundles covered with the sheet of fibroblasts was prepared, and the plurality of nerve bundles was covered by rolling with a large fibroblast sheet formed in advance on a petri dish, thereby obtaining an implant. Then, the implant was transplanted as described below.

Example 7: Transplantation of Nerve Bundle 1 (Transplantation into Rat Sciatic Nerve)

The nerve bundle implant formed in Example 6 was transplanted into the sciatic nerve in rats according to the following method.

Rats (nude rats; F344/NJcl-rnu/rnu, 15-week-old, male, available from CLEA Japan, Inc.) were subjected to general anesthesia by intraperitoneal administration of three types of mixed anesthetic agents (a mixture of medetomidine hydrochloride (0.15 mg/0.15 ml/kg), midazolam (2 mg/0.4 ml/kg), butorphanol tartrate (2.5 mg/0.5 ml/kg), and physiological saline (1.45 ml/kg)), and a part of the sciatic nerve was excised. Each of the two ends of the nerve bundle implant formed in Example 6 (about 1 cm in length, about 1 mm in diameter) was sutured to each of the two nerve stumps after sciatic nerve excision with 3 stitches of surgical sutures (10-0 nylon), and the nerve bundle implant was transplanted into the excised sciatic nerve portion. On day 14 after transplantation, the nerve bundle implant was joined to the rat sciatic nerve, and no necrosis of the nerve bundle implant was observed. The photograph of the transplanted site immediately after transplantation and the photograph of the transplanted site on day 14 after transplantation of the nerve bundle implant are shown in FIG. 5 (A: immediately after transplantation, B: on day 14 after transplantation). Further, when the follow-up of the rats after transplantation of the nerve bundle implant was observed, the toes were sufficiently open and became active similarly to autologous nerve-transplanted rats as controls. Furthermore, there were no influences such as lifetime shortening. These results indicated that the transplanted nerve bundle implant functions on behalf of the excised sciatic nerve.

Example 8: Immunofluorescence Staining of Nerve Bundle 1

The nerve bundle formed in Example 6 was fixed with 4% paraformaldehyde, and immunofluorescence staining was performed with p75NTR and S100 to confirm the presence or absence of expressions of p75NTR and S100. Then, the nerve bundle was cut parallel to the extension direction of axons of neurons. Each photograph of the cut surface (vertical cross-section) of the cut nerve bundle is shown in FIG. 6. The photographs in FIGS. 6A to 6C show the expressions of S100, p75NTR, and DAPI, respectively. The photograph of FIG. 6D is a merged photograph of FIGS. 6A to 6C. In the nerve bundle, expressions of p75NTR and S100 along the extension direction of axons of neurons were recognized from the photographs of FIG. 6.

Example 9: Immunofluorescence Staining of Nerve Bundle 2

Figures 7A, 7B, 7C, 7D, 7E:
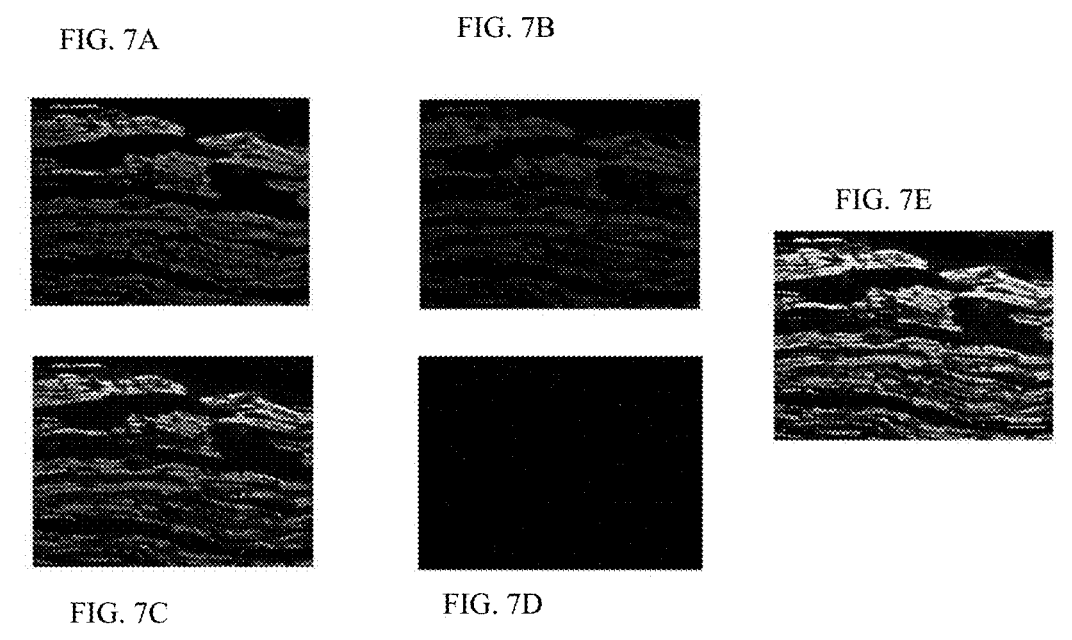

The nerve bundle formed in Example 6 was fixed with 4% paraformaldehyde, and immunofluorescence staining was performed with HNK-1 carbohydrate, p75NTR, and MPZ to confirm the presence or absence of expressions of HNK-1 carbohydrate, p75NTR, and MPZ. Then, the nerve bundle was cut parallel to the extension direction of axons of neurons. Each photograph of the cut surface (vertical cross-section) of the cut nerve bundle is shown in FIG. 7. The photographs in FIGS. 7A to 7D show the expressions of HNK-1 carbohydrate, p75NTR, MPZ, and DAPI, respectively. FIG. 7E is a merged photograph of FIGS. 7A to 7D. In the nerve bundle, expressions of HNK-1, p75NTR, and MPZ along the extension direction of axons of neurons were recognized from the photographs of FIGS. 7A to 7C. From the photograph of FIG. 7E, it was further confirmed that HNK-1, p75NTR, and MPZ were expressed in approximately the same position. MPZ is known as a marker for myelin sheath, particularly immature myelin sheath. Thus, it was suggested from the photograph of FIG. 7E that the nerve bundle included neuronal cells with myelin sheath and that HNK-1 and p75NTR were expressed in the myelin sheath.

Example 10: Immunofluorescence Staining of Nerve Bundle 3

The nerve bundle formed in Example 6 was fixed with 4% paraformaldehyde, and immunofluorescence staining was performed with NF200 and myelin basic protein to confirm the presence or absence of expressions of NF200 and myelin basic protein. Then, the nerve bundle was cut at a right angle to the extension direction of axons of neurons. A photograph of the cut surface (cross section) of the cut nerve bundle is shown in FIG. 8. Expressions of NF200 and myelin basic protein around the NF200 were recognized from the photograph of FIG. 8. NF200 is known as a neuronal marker for myelinated nerves, and the myelin basic protein is known as a marker for Schwann cells. Thus, it was suggested from the photograph of FIG. 8 that the nerve bundle included neuronal cells with the myelin sheath of Schwann cells.

Example 11: Immunofluorescence Staining of Nerve Bundle 4

The nerve bundle formed in Example 6 was fixed with 4% paraformaldehyde, and immunofluorescence staining was performed with NF200, S100, and peripherin to confirm the presence or absence of expressions of NF200, S100, and peripherin. Then, the nerve bundle was cut at a right angle to the extension direction of axons of neurons. Each photograph of the cut surface (cross section) of the cut nerve bundle is shown in FIG. 9. The photograph of FIG. 9A shows the expressions of NF200 and S100. FIG. 9B shows the expressions of S100 and peripherin. Expressions of NF200 and S100 around the NF200 were recognized from the photograph of FIG. 9A. NF200 is known as a neuronal marker for myelinated nerves and S100 is known as a marker for Schwann cells. Thus, it was suggested from the photograph of FIG. 9A that the nerve bundle included neurons with the myelin sheath of Schwann cells. Further, expressions of peripherin and S100 around the peripherin were recognized from the photograph of FIG. 9B. Peripherin is primarily known as a neuronal marker for the peripheral nervous system. Thus, it was suggested from FIG. 9B that the nerve bundle included neurons with the myelin sheath of Schwann cells.

Example 12: Immunofluorescence Staining of Nerve Bundle 5

The nerve bundle formed in Example 6 was fixed with 4% paraformaldehyde, and immunofluorescence staining was performed with NF200 and the periaxin to confirm the presence or absence of expressions of NF200 and periaxin. Then, the nerve bundle was cut at a right angle to and parallel to the extension direction of axons of neurons. A photograph of the cut surface (cross section) of the cut nerve bundle is shown in FIG. 10A. Each photograph of the cut surface (vertical cross section) of the cut nerve bundle is shown in FIGS. 10B and 10C. Expressions of NF200 and periaxin around the NF200 were recognized from the photograph of FIG. 10A. Further, expressions of NF200 and periaxin along the extension direction of axons of neurons were recognized from the photographs of FIGS. 10B and 10C. NF200 is known as a neuronal marker for myelinated nerves and periaxin is known as a marker for Schwann cells. Thus, it was suggested from the photographs of FIGS. 10A to 10C that the nerve bundle included neurons with the myelin sheath of Schwann cells.

Example 13: Immunofluorescence Staining of Nerve Bundle 6

The nerve bundle formed in Example 6 was fixed with 4% paraformaldehyde, and immunofluorescence staining was performed with CD31 and PDGFRβ to confirm the presence or absence of expressions of CD31 and PDGFRβ. Then, the nerve bundle was cut at a right angle to the extension direction of axons of neurons. Each photograph of the cut surface (cross section) of the cut nerve bundle is shown in FIGS. 11A and 11B. Expressions of CD31 and PDGFRβ around neurons (axons) of the nerve bundle were recognized from the photographs of FIGS. 11A and 11B. CD31 is known as a marker for vascular endothelial cells, and PDGFRβ is known as a marker for vascular pericytes and fibroblasts. Thus, it was suggested from the photographs of FIGS. 11A to 11B that the nerve bundle included a pericyte or fibroblast layer around the axons of the neurons and included a tube of vascular endothelial cells present in the layer.

Example 14: Immunofluorescence Staining of Nerve Bundle 7

The nerve bundle formed in Example 6 was fixed with 4% paraformaldehyde, and immunofluorescence staining was performed with CD31 and PDGFRβ to confirm the presence or absence of expressions of CD31 and PDGFRβ. Then, the nerve bundle was cut at a right angle to the extension direction of axons of neurons. Each photograph of the cut surface (cross section) of the cut nerve bundle is shown in FIG. 12. FIG. 12A is a partially enlarged photograph of the cut surface (cross section) of the nerve bundle, and FIG. 12B is an enlarged photograph of a site where particularly strong expressions of CD31 and PDGFRβ are observed in the photograph of FIG. 12A. It was confirmed from the photographs in FIGS. 12A and 12B that CD31 was expressed in a circular form, and further, PDGFRβ was expressed so as to surround the circle of CD31. CD31 is known as a marker for vascular endothelial cells, and PDGFRβ is known as a marker for vascular pericytes and fibroblasts. Thus, it was suggested from the photographs of FIGS. 12A to 12B that the nerve bundle included a pericyte or fibroblast layer around the axons of the neurons and had a tube of vascular endothelial cells present in the layer, and further, the tube of vascular endothelial cells was lined with vascular pericytes and/or fibroblasts.

Example 15: Immunofluorescence Staining of Nerve Bundle 8

FIG. 13 shows an enlarged photograph of a site where particularly strong expressions of CD31 and PDGFRβ are observed in the cut surface (cross section) of another nerve bundle that has been subjected to immunofluorescence staining and cutting in a similar manner to Example 14. It was confirmed from the photograph in FIG. 13 that CD31 was expressed in a circular form, and further, PDGFRβ was expressed so as to surround the circle of CD31. Thus, it was suggested from the photograph of FIG. 13 that the nerve bundle included a pericyte or fibroblast layer around the axons of the neurons and included a tube of vascular endothelial cells present in the layer, and further, the tube of vascular endothelial cells was lined with vascular pericytes and/or fibroblasts.

Example 16: Transplantation of Nerve Bundle 2 (Transplantation into Rat Sciatic Nerve)

A rat in which the sciatic nerve had been transplanted (autotransplanted) with the nerve bundle implant formed in Example 6 according to the method similar to Example 7 (nerve bundle implant-transplanted rat) was prepared. A rat in which the distal and proximal ends of the excised nerve had been inverted and transplanted according to the similar method described above (autologous nerve-transplanted rat) as well as a rat transplanted with an artificial nerve (Ner-bridge (trade name), available from TOYOBO CO., LTD.) were prepared. Further, a rat in which the sciatic nerve had been incised (sciatic nerve-incised rat) was prepared. Photographs of the transplanted sites and the incised site in the rats 12 weeks after transplantation are shown in FIG. 14 (A: autologous nerve-transplanted rat; B: nerve bundle implant-transplanted rat; C: artificial nerve-transplanted rat; D: sciatic nerve-incised rat). The photographs of FIG. 14 showed that the transplanted autologous nerve, the transplanted nerve bundle implant, and the transplanted artificial nerve were joined to the sciatic nerve of the autologous nerve-transplanted rat, the sciatic nerve of the nerve bundle implant-transplanted rat, and the sciatic nerve of the artificial nerve-transplanted rat, respectively. Further, in the case where the nerve bundle implant was transplanted (FIG. 14B), the nerve bundle was significantly covered with fibroblasts as compared with the case where the autologous nerve was transplanted or the case where the artificial nerve was transplanted (FIGS. 14A and 14C).

In addition, 6 autologous nerve-transplanted rats, 3 nerve bundle implant-transplanted rats, 4 artificial nerve-transplanted rats, and 4 sciatic nerve-incised rats were prepared, and changes in the sciatic functional index (SFI) after transplantation (or after incision) in each of the rats were observed. Note that the sciatic functional index is described in the reference "Bain et al., Plast Reconstr Surg 83: 129-139 (1989)". The sciatic functional index was calculated from the footprints obtained by allowing each rat with inked volar pads to walk, based on the mathematical formula shown in FIG. 15A. FIG. 15B shows temporal changes in the sciatic functional index in each of the rats. FIG. 15B showed that the sciatic functional index 6 weeks after transplantation increased in the autologous nerve-transplanted rats, nerve bundle implant-transplanted rats, and artificial nerve-transplanted rats, as compared with the sciatic functional index immediately after transplantation. It was also shown that, in the autologous nerve-transplanted rats and the nerve bundle implant-transplanted rats, the sciatic functional index 12 weeks after transplantation further increased as compared with the sciatic functional index 6 weeks after transplantation.

Concerning each of the rats after calculation of the sciatic functional index, the wet weight of the gastrocnemius muscle at the distal end of the transplanted site was excised in the 12th week after transplantation (or after incision), and a ratio of the wet weight after excision to the wet weight of the gastrocnemius muscle in the rat with non-excised sciatic nerve was used for measurement. The measurement results are shown in FIG. 16. FIG. 16 showed that the weight of the gastrocnemius muscle in the autologous nerve-transplanted rats, nerve bundle implant-transplanted rats, and artificial nerve-transplanted rats was larger than the weight of the gastrocnemius muscle in the sciatic nerve-incised rats; and the autologous nerve, the nerve bundle implant, and the artificial nerve each served as the rat sciatic nerve.

Example 17: Immunostaining of Nerve Bundle after Transplantation into Rat Sciatic Nerve The nerve bundle implant transplanted into the rat sciatic nerve in Example 16 was excised 12 weeks after transplantation. The excised nerve bundle implant was fixed with 4% paraformaldehyde, and immunofluorescence staining was performed with STEM121, p75NTR, and MPZ to confirm the presence or absence of expressions of STEM121, p75NTR, and MPZ. Then, the nerve bundle implant was cut at a right angle to the extension direction of axons of neurons. Each photograph of the cut surface (cross section) of the cut nerve bundle implant is shown in FIG. 17. The photographs in FIGS. 17A to 17D show the expressions of STEM121, p75NTR, DAPI, and MPZ, respectively. FIG. 17E is a merged photograph of FIGS. 17A to 17D. It was recognized from the photographs of FIGS. 17A, 17B, and 17D that STEM121, p75NTR, and MPZ were expressed at approximately the same position. STEM121 shows neurons in the nerve bundle implant. Consequently, this suggested that p75NTR and MPZ were expressed in the nerve bundle in the nerve bundle implant, particularly neurons.

INDUSTRIAL APPLICABILITY

According to the present invention, it is possible to efficiently extend and enlarge axons of neural cells. As a result, a nerve bundle having axons with a length and diameter sufficient for transplantation can be efficiently formed, allowing for efficient provision of a nerve bundle implant necessary for nerve transplantation.

REFERENCE SIGNS LIST

1 Nerve bundle forming device
2 Dimethylpolysiloxane substrate
3 Recess
4 Channel portion

The invention claimed is:

1. A method of producing a cultivated neural tissue with a first set of length and width, the method comprising culturing a neural cell population differentiated from oral mesenchymal cells on a substrate surface,
    wherein a portion of the surface is covered by feeder cells before culturing,
    wherein the portion of the surface corresponds to a second set of length and width,
    wherein the feeder cells promote the neural cell population to grow into a cultured basic tissue with the second set of length and width through the culturing,
    wherein the cultivated tissue is produced by combining a plurality of the cultured basic tissues so that the width of the cultivated tissue is larger than the width of the cultured basic tissue.

2. The method according to claim 1, wherein the cultivated tissue and the cultured basic tissue are elongated nerve bundles of fibers consisting of axons and blood vessels, and wherein the feeder cells are selected from vascular component cells and perivascular cells to extend axons of neural cells.

3. The method according to claim 2, wherein the feeder cells include at least one type of cells selected from the group consisting of pericytes, vascular endothelial cells, fibroblasts, oligodendrocytes, and Schwann cells.

4. The method according to claim 2, wherein the feeder cells include cells secreting at least one type of growth factor selected from the group consisting of VEGF, NGF, BDNF, FGF-2, NGFB, and EGF.

5. The method according to claim 2, wherein the nerve bundle includes a myelin sheath containing Schwann cells.

6. The method according to claim 2, further comprising:
    (a) preparing a substrate including at least one recess and a channel portion connected to the recess, the channel portion being covered with the feeder cells;
    (b) adding the neural cell population to the recess; and
    (c) cultivating the neural cell population to extend axons of neural cells along the channel portion.

7. The method according to claim 2, further comprising:
    (a) preparing a substrate including two recesses and a channel portion connecting the two recesses, the channel portion being covered with the feeder cells;

(b) adding the neural cell population to the recesses; and
    (c) cultivating the neural cell population to extend axons of neural cells along the channel portion.

8. The method according to claim 7, wherein, in the step (a), the channel portion is covered with fibroblasts before being covered with the feeder cells.

9. The method according to claim 2, wherein the neural cell population further includes endothelial cells.

10. The method according to claim 9, wherein the endothelial cells included in the neural cell population are derived from blood vessels.

11. The method according to claim 10, wherein the endothelial cells are derived from at least one tissue selected from the group consisting of a dental pulp, a gingiva, a subcutaneous tissue, a coelomic artery, a coelomic vein, and an umbilical cord.

12. The method according to claim 10, wherein the blood vessels have a tube comprising endothelial cells surrounded by vascular pericytes or fibroblasts.

13. The method according to claim 9, wherein the neural cells of the neural cell population and the endothelial cells are derived from an identical individual.

14. The method according to claim 9, wherein a portion of the neural cells of the neural cell population and a portion of the endothelial cells of the neural cell population are each on surfaces of particles of biocompatible material.

15. The method according to claim 14, wherein the biocompatible material includes collagen.

16. The method according to claim 14, wherein the biocompatible material includes collagen beads.

17. The method according to claim 7, wherein the channel portion has a length of 3 mm or greater.

18. The method according to claim 2, wherein a plurality of the cultured basic tissues of nerve bundles are combined and wrapped together with a cover sheet of a biocompatible material to form the cultivated tissue comprising a roll of the combined cultured basic tissues of nerve bundles.

19. The method according to claim 18, wherein the sheet contains fibroblasts.

20. The method according to claim 18, wherein the cultivated tissue is a nerve regeneration implant.

21. The method according to claim 2, wherein the blood vessel is present along the axons and comprises a tube of endothelial cells, and wherein the nerve bundle comprises at least one type of cells selected from HNK-1 carbohydrate-expressing cells and p75NTR-expressing cells.

22. The method according to claim 21, wherein the nerve bundle comprises HNK-1 carbohydrate-expressing cells and p75NTR-expressing cells.

23. The method according to claim 21, wherein the nerve bundle comprises at least one type of cells selected from the group consisting of NF200-expressing cells, peripherin-expressing cells, myelin basic protein-expressing cells, S100-expressing cells, MPZ-expressing cells, periaxin-expressing cells, CD31-expressing cells, and PDGFRβ-expressing cells.

24. The method according to claim 21, wherein the nerve bundle comprises: NF200-expressing cells; peripherin-expressing cells; myelin basic protein-expressing cells; S100-expressing cells; MPZ-expressing cells; periaxin-expressing cells; CD31-expressing cells; and PDGFRβ-expressing cells.

25. The method according to claim 18, wherein the sheet is a cell layer that covers the axons, wherein the cell layer comprises either fibroblasts or pericytes and wherein a tube of endothelial cells is present in the cell layer.

26. The method according to claim 14, wherein the particle on which the neural cells are attached is separately prepared from the particles on which the endothelial are attached before the culturing, so that the particles, on which the endothelial cells are attached, fuse one another during the culturing, resulting in efficient formation of hollow blood vessel tubes where the inner surface of the tube is covered by endothelial cells, and where the inner space of the tube is filled by the biocompatible material, thus facilitating the growth of the endothelial cells by ingestion of the biocompatible material in the inner-tube space.

27. The method according to claim 26, wherein the particle on which the endothelial cells are attached comprises biocompatible material that includes erythrocytes inside the particle, so that the formed hollow blood vessels contain erythrocytes inside the inner space of the tube, thus preventing necrosis of the nerve bundle due to oxygen supplied by the erythrocytes.

\* \* \* \* \*